US006649411B2

(12) United States Patent
Gozes et al.

(10) Patent No.: US 6,649,411 B2
(45) Date of Patent: *Nov. 18, 2003

(54) METHODS OF INHIBITING CANCER CELLS WITH ADNF III ANTISENSE OLIGONUCLEOTIDES

(75) Inventors: Illana Gozes, Ramat-Hasharon (IL); Douglas E. Brenneman, Damascus, MD (US); Rachel Zamostiano, Hod-Hasharon (IL); Edgar Gelber, Petach-Tikvah (IL); Albert Pinhasov, Tel-Aviv (IL); Merav Bassan, Netanya (IL)

(73) Assignees: The United States of America as represented by the Department of Health and Human Services, Washington, DC (US); Ramot at Tel-Aviv University Ltd., Tel-Aviv (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/364,609

(22) Filed: Jul. 30, 1999

(65) Prior Publication Data

US 2003/0036521 A1 Feb. 20, 2003

(51) Int. Cl.$^7$ .............................. C12N 5/00; C12Q 1/68; C12P 19/34; C07H 21/02; C07H 21/04

(52) U.S. Cl. ........................ 435/375; 435/6; 435/91.1; 435/377; 435/455; 536/23.1; 536/24.5

(58) Field of Search .................. 435/6, 91.1, 91.31, 435/91.5, 91.51, 455, 325, 366, 377; 536/23.1, 24.5, 25.3; 514/44

(56) References Cited

U.S. PATENT DOCUMENTS 5,525,468 A * 6/1996 McSwiggen .................... 435/6
5,767,240 A * 6/1998 Brenneman et al. ........ 530/350
5,801,154 A * 9/1998 Baracchini et al. ........... 514/44

FOREIGN PATENT DOCUMENTS

WO   WO 92/18140   * 10/1992   .......... A61K/37/00
WO   WO 96/11948   * 4/1996    .......... C07K/14/475
WO   WO 98/35042   8/1998

OTHER PUBLICATIONS

Crooke, S.T. 1998 Antisense Research & Application. Chapter 1, pp 1–50. Publish. by Springer.*
Branch, A 1998 Trends in Bioch. Sci (TIBS) vol. 23, pp 45–50.*
Glazner et al., "Activity–dependent neurotrophic factor: a potent regulator of embryonic growth and development," Anat Embryol (1999) 200:65–71.

Milner et al., "Selecting effective antisense reagents on combinatorial oligonucleotide arrays," Nature Biotechnology (1997) 15:537–541.
Zamostiano et al., "Cloning and Characterization of the Human Activity–dependent Neuroprotective Protein," The Journal of Biological Chemistry (2001) 276:708–714.
Bassan, M. et al. "VIP–Induced Mechanism of Neuroprotection: The Complete Sequence of a Femtomolar–Acting Activity–Dependent Neuroprotective Protein." *Regulatory Peptides*, 71(2):, Aug. 15, 1997.*
Bassan, M. et al. "Complete Sequence of a Novel Protein–Containing a Femtomolar–Activity–Dependent Neuroprotective Peptide." *Journal of Neurochemistry* 72:1283–1293 (1999).*
Beni–Adani, L. et al. "Activity–Dependent Neurotrophic Protein is Neuroprotective in a Mouse Model of Closed Head Injury." Society for Neuroscience, 28$^{th}$ Annual Meeting, Los Angeles, CA, Nov. 7–12, 1998. *Abstracts* 23(1):1043 (1998).*
Brenneman, D.C. and Gozes, I. "A Femtomolar–Acting Neuroprotective Peptide." *Journal of Clinical Investigation* 97:229–230 (1996).*
Brenneman, D.E. et al. "Identification of a Nine Amino Acid Core Peptide from Activity Dependent Neurotrophic Factor I." Society for Neuroscience, 27$^{th}$ Annual Meeting, New Orleans, LA, Oct. 25–30, 1997. *Abstracts* 23(2): 2250 (1997).*
Brenneman, D.E. et al. "Activity–Dependent neutotrophic Factor: Structure–Activity Relationships of Femtomolar–Acting Peptides." *Journal of Pharmacology and Experimental Therapeutics* 285: 619–627 (1998).*
Davidson, A. et al. "Protection Against Developmental Retardation and Learning Impairments in Apolipoprotein E–Deficient Mice by Activity–Dependent Femtomolar–Acting Peptides." Society for Neuroscience, 27$^{th}$ Annual Meeting, New Orleans, LA, Oct. 25–30, 1997. *Abstracts* 23(2)2250 (1997).*
Dibbern, D.A., Jr. et al. "Inhibition of Murine Embryonic Growth by Human Immunodeficiency Virus Envelope Protein and Its Prevention by Vasoactive Intestinal Peptide and Activity–Dependent Neurotrophic Factor." *Journal of Clinical Investigation* 99: 2837–2841 (1997).*
Giladi, E. "Protection Against Developmental and Learning Impairments in Apolipoprotein E–Deficient Mice by Activity–Dependent Femtomolar–Acting Peptides." *Neuroscience Letters* Supplement 48 S1–S60, P. S19 (1997).*

(List continued on next page.)

Primary Examiner—Sean McGarry
Assistant Examiner—Jane Zara
(74) Attorney, Agent, or Firm—Townsend and Townsend and Crew LLP

(57) ABSTRACT

The present invention provides methods of using antisense ADNF III oligonucleotides to inhibit the growth of pathologically proliferating cells. The invention also provides methods and kits for using ADNF III nucleic acid probes to detect the presence of pathologically proliferating cells in human tissues.

13 Claims, 9 Drawing Sheets

OTHER PUBLICATIONS

Glazner, G.W. et al. "A 9 Amino Acid Peptide Fragment of Activity–Dependent Neurotrophic Factor (ADNF) Protects Neurons from Oxidative Stress–Induced Death." Society for Neuroscience, 27th Annual Meeting, New Orleans, LA, Oct. 25–30, 1997. *Abstracts* 23(2)2249 (1997).*

Gozes, I. et al. "Stearyl–Norleucine–Vasoactive intestinal Peptide (VIP): A novel VIP Analog for Noninvasive Impotence Treatment." *Endocrinology* 134: 2125 (1994).*

Gozes, I. et al. "Superactive Lipophilic Peptides Discriminate Multiple Vasoactive intestinal Peptide Receptors." *Journal of Pharmacology and Experimental Therapeutics* 27:3161–167 (1995).*

Gozes, I. et al. "Neuroprotective Strategy for Alzheimer Disease: Intranasal Administration of a Fatty Neuropeptide." *Proc. Natl. Acad. Sci. USA* 93:427–432 (1996).*

Gozes, I. and Brenneman, D.E. "Activity–Dependent Neurotrophic Factor (ADNF)." *Journal of Molecular Neuroscience* 7:235–244 (1996).*

Gozes, I. et al. "Protection Against Developmental Retardation in Apolipoprotein E–Deficient Mice by a Fatty neuropeptide: Implications for Early Treatment of Alzheimer's Disease." *Journal of Neurobiology* 33:329–342 (1997).

Gozes I. et al. "Antiserum to Activity–Dependent Neurotrophic Factor Produces Neuronal Cell Death in CNS Cultures: Immunological and Biological Specificity." *Developmental Brain Research* 99:167–175 (1997).

Gozes, I. et al. "The cDNA Structure of a Novel Femtomolar–Acting Neuroprotective Protein: Activity–Dependent–Neurotrophic Factor III (ADNFIII)." Society for Neuroscience, 27th Annual Meeting, New Orleans, LA, Oct. 25–30, 1997. *Abstracts* 23(2):2250 (1997).

Gozes, I. et al. A Femtomolar–Acting Activity–Dependent Neuroprotective Protein (ADNP). *Neuroscience Letters* Supplement 48 S1–S60, p. S21 (1997)–.

Hill, J.M. et al. "Learning Impairment in Adult Mice Produced by Early Embryonic Administration of Antiseum to Activity–Dependent Neurotrophic Factor (ADNF)." Society for Neuroscience, 27th Annual Meeting, New Orleans, LA, Oct. 25–30, 1997. *Abstracts* 23(2):2250 (1997).

Lilling, G. et al. "Inhibition of Human Neuroblastoma Growth by a Specific VIP Antagonist." *Journal of Molecular Neuroscience* 5: 231–239 (1995).

McKune, S.K. et al. "Localization of mRNA for Activity-Dependent Neurotrophic Factor III (ADNF III) in mouse Embryo and Adult CNS." Society for Nueroscience, 27th Annual Meeting, New Orleans, LA, Oct. 25–30, 1997. *Abstracts* 23(2):2249 (1997).

Nelbock, P. et al. A cDNA for a Protein that Interacts with the Human Immunodeficiency Virus Tat Transactivator. *Science*, 248:1650–1653 (1990).

Pelsman, A. et al. "In Vitro Degeneration of Down Syndrome neurons is Prevented by Activity–Dependent Neurotrophic Factor–Derived Peptides." Society for Neuroscience, 28TH Annual Meeting, Los Angeles, CA, Nov. 7–12, 1998. *Abstracts* 24:1044 (1998).

Brenneman et al. "Neuronal Cell Killing by the Envelope Protein of HIV and Its Prevention by Vasoactive Intestinal Peptide." *Nature* 335:636 (1988).

Brenneman et al. "N–Methyl–D–Aspartate Receptors Influence Neuronal Survival in Developing Spinal Cord Cultures" *Dev. Brain Res*. 51:63 (1990).

Glazner, G.W. et al. "Activity Dependent Neurotrophic Factor: A Potent Regulator of Embryonic Growth." *Anat. Embryol.*. 200:65–71 (1999).

Gressens, P. et al. "Growth factor function of vasoactive intestinal peptide in whole cultured mouse embyros." *Nature*, 362:155–58 (1993).

* cited by examiner

Human ADNP cDNA (H7)
Exon I
```
  1  ATGTTCCAACTTCCTGTCAACAATCTTGGCAGTTTAAGAAAAAGCCCGAAAACTGTGAAAAAATACTTAGTGAC   25
     M  F  Q  L  P  V  N  N  L  G  S  L  R  K  A  R  K  T  V  K  K  I  L  S  D
                                        ExonII →
 76  ATTGGGTTGGAATACTGTAAAGAACATATAGAAGATTTTAAACAATTTGAACCTAATGACTTTTATTTGAAAAAC   50
     I  G  L  E  Y  C  K  E  H  I  E  D  F  K  Q  F  E  P  N  D  F  Y  L  K  N
                                                                    ExonIII →
151  ACTACATGGGAGGATGTAGGACTGTGGGACCCATCACTTACGAAAAACCAGGACTATCGGACAAAACCTTTCTGC   75
     T  T  W  E  D  V  G  L  W  D  P  S  L  T  K  N  Q  D  Y  R  T  K  P  F  C
226  TGCAGCGCTTGTCCATTTCCTCAAAATTCTCTGCTACAAAAGTCATTTCCGCAATGTCCATAGTGAAGAC   100
     C  S  A  C  P  F  S  K  F  S  A  Y  K  S  H  F  R  N  V  H  S  E  D
301  TTTGAAAATAGAATTCTCCTTAATTGCCCCTACTGTACCTTCAATGCAGACAAAAAGACTTTGGAAACACATT   125
     F  E  N  R  I  L  L  N  C  P  Y  C  T  F  N  A  D  K  K  T  L  E  T  H  I
376  AAAATATTTCATGCTCCAGGCTGACAGTAGCAGCCTCAGCACTTTCAAAGATAAAAACAAAAATGAT   150
     K  I  F  H  A  P  N  A  S  A  P  S  S  S  L  S  T  F  K  D  K  N  K  N  D
451  GGCCTTAAACCTAAGCAGGCTGACAGTGTAGAGCAAGCTGTTTATTACTGTAAGAAGTGCACTTACCGAGATCCT   175
     G  L  K  P  K  Q  A  D  S  V  E  Q  A  V  Y  Y  C  K  K  C  T  Y  R  D  P
526  CTTTATGAAATAGTTAGGAAGCACATTTACAGGGAACATTTCAGCATGTGGCAGCACCTTACATAGCAAAGGCA   200
     L  Y  E  I  V  R  K  H  I  Y  R  E  H  F  Q  H  V  A  A  P  Y  I  A  K  A
601  GGAGAAAAATCACTCAATGGGGCAGTCCCCTTAGGCTCGAATGCCCGAGAAGAGAGTATTCACTGCAAGCGA   225
     G  E  K  S  L  N  G  A  V  P  L  G  S  N  A  R  E  E  S  I  H  C  K  R
676  TGCCTTTCATGCCAAAGTCCTATGAAGCTTGGTACAGCATGTCATCGAAGACCATGAACGTATAGGCTATCAG   250
     C  L  F  M  P  K  S  Y  E  A  L  V  Q  H  V  I  E  D  H  E  R  I  G  Y  Q
751  GTCACTGCCATGATTGGGCACACAAATGTAGTGGTTCCCGATCCAAACCCTGATGCTAATTGCTCCCAAACCT   275
     V  T  A  M  I  G  H  T  N  V  V  P  R  S  K  P  L  M  L  I  A  P  K  P
826  CAAGACAAGAAGAGCATGGGACTCCCACCAAGGATCGGTTCCTTGCTTCTGGAAATGTCCGGTCTTTACCATCA   300
     Q  D  K  K  S  M  G  L  P  P  R  I  G  S  L  A  S  G  N  V  R  S  L  P  S
```

FIG. 4

```
901   CAGCAGATGGTGAATGCACTCTCAATACCAAAGCCTAACTTAAATTCTACAGGAGTCAACATGATGTCCAGTGTT   325
      Q  Q  M  V  N  R  L  S  I  P  K  P  N  L  N  S  T  G  V  N  M  M  S  S  V
                                                                      67    68

976   CATCTGCAGCAGAACAACTATGGAGTCAAATCTGTAGGCCAGGGTTACAGTGTTGGTCAGTCAATGAGACTGGGT   350
      H  L  Q  Q  N  N  Y  G  V  K  S  V  G  Q  G  Y  S  V  G  Q  S  M  R  L  G

1051  CTAGGTGGCAACGCACCAGTTTCCATTCCTCAACAATCTGTAAAGCAGTTACTTCCAAGTGGAAACGGA        375
      L  G  G  N  A  P  V  S  I  P  Q  Q  S  V  K  Q  L  L  P  S  G  N  G

1126  AGGTCTTATGGGCTTGGGTCAGTGAGCAGAGGTCCCAGGCACCAAGATACTCCCCTGCAGTCTGCTAATGCCTCT    400
      R  S  Y  G  L  G  S  E  Q  R  S  Q  A  P  A  R  Y  S  L  Q  S  A  N  A  S

1201  TCTCTCTCATCGGGCCAGTTAAAGTCTCCTTCCCCCAGTAACACTTCCTCAGTCAGAGTGTTAGGTCAGTCCAGT    425
      S  L  S  S  G  Q  L  K  S  P  S  L  S  Q  S  Q  A  S  R  V  L  G  Q  S  S

1276  TCCAAACCTGCTGCAGCAGCTACTGGACCCCCACAGGCCCCCCAGTAACACTTCCTCAACTCAAAAGTGAAAATATGTACA   450
      S  K  P  A  A  A  A  T  G  P  P  P  G  N  T  S  S  T  Q  K  W  K  I  C  T

1351  ATCTGTAATGAGCTTTTCCTGAAAATGTCTATAGTGTGCACTTCGAAAAGAACATAAAGCTGAGAAAGTCCCA     475
      I  C  N  E  L  F  P  E  N  V  Y  S  V  H  F  E  K  E  H  K  A  E  K  V  P

1426  GCAGTAGCCAACTACATTATGAAAATACACACAATTTACTAGCAAATGCCTCTACTGTAATCGCTATTTACCACA    500
      A  V  A  N  Y  I  M  K  I  H  N  F  T  S  K  C  L  Y  C  N  R  Y  L  P  T

1501  GATACTCTGCTCAACATATGTTAATTCATGGTCTCTGTCCATATTGCCGTTGCAACTTTCAATGATGTGGAA      525
      D  T  L  L  N  H  M  L  H  G  L  S  C  P  Y  C  R  S  T  F  N  D  V  E
                                                              ->

1576  AAGATGGCCCGCACACATGCGGATGGTTCACATTGATGAAGAGATCTACTTTGAGTTTT                   550
      K  M  A  A  H  M  R  M  V  H  I  D  E  E  M  G  P  K  T  D  S  T  L  S  F
         <-

1651  GATTTGACATTGCAGCAGGGGTAGTCACACTAACACATCATCTCCTGGTAACTACATACAATCTGAGGGATGCCCA   575
      D  L  T  L  Q  Q  G  S  H  T  N  I  H  L  L  V  T  T  Y  N  L  R  D  A  P

1726  GCTGAATCTGTTGCTTACCATGCCCAAAATAATCCTCCAGTTCCTCCAAAGCCAAAGGTTCAGGAAAAG          600
      A  E  S  V  A  Y  H  A  Q  N  N  P  P  V  P  P  K  P  Q  P  K  V  Q  E  K

1801  GCAGATATCCCTGTAAAAAAGGATGTTGGGAAAACCCTTTGTCCT                                  625
      A  D  I  P  V  K  S  S  P  Q  A  A  V  P  Y  K  K  D  V  G  K  T  L  C  P
```

FIG. 4 (CONTINUED)

```
1876  CTTTGCTTTTCAATCCTAAAAGGACCCATATCTGATGCACTTGCACATCACTTACGAGAGAGGCACCAAGTTATT
       L  C  F  S  I  L  K  G  P  I  S  D  A  L  A  H  H  L  R  E  R  H  Q  V  I    650
1951  CAGACGGTTCATCATCCAGTTGAGAAAAAGCTTCATTGCCTTGGTGTATACCAGCAACATG
       Q  T  V  H  P  V  E  K  K  L  T  Y  K  C  I  H  C  L  G  V  Y  T  S  N  M    675
2026  ACCGCCTCAACTATCACTCTGCATCTAGTTCACTGCAGGGGCGTTGGAAAGACCCAAAATGGCCAGGATAAGACA
       T  A  S  T  I  T  L  H  L  V  H  C  R  G  V  G  K  T  Q  N  G  Q  D  K  T    700
2101  AATGCACCCTCTCGGCTTAATCAGTCTCCAAGTCTGGCACTTGTGAAGCGCACTTACGAGCAAATGGAATTTCCC
       N  A  P  S  R  L  N  Q  S  P  S  L  A  P  V  K  R  T  Y  E  Q  M  E  F  P    725
2176  TTACTGAAAAACGAAAGTTAGATGATAGTGATTCACCCAGCTTCTTTGAAGAGAAGCCTGAAGAGCCTGTT
       L  L  K  K  R  K  L  D  D  S  D  S  P  S  F  F  E  E  K  P  E  E  P  V    750
2251  GTTTTAGCTTTAGACCCCATATCCCCACCAGGGTCATGAAGATGATGATTCCTATGAAGCCAGGAGAGATTCC
       V  L  A  L  D  P  K  G  H  E  D  D  S  Y  E  A  R  K  S  F  L  T  K  Y  F    775
2326  AACAAACAGCCCTATTTTAGTAACAAGAATTAAATAAAGTGTCCCGTGATTGTGAAAAGTACAAGCCTGGTGTTGCTGGGG
       N  K  Q  P  Y  P  T  R  R  E  I  E  K  L  A  A  S  L  W  L  W  K  S  D  I    800
2401  GCTTCCCATTTTAGTAACAAGAATTAAATAAAGTGTCCCGTGATTGTGAAAAGTACAAGCCTGGTGTTGCTGGGG
       A  S  H  F  S  N  K  R  K  K  C  V  R  D  C  E  K  Y  K  P  G  V  L  L  G    825
2476  TTTAACATGAAGGAATTAAATAAAGTGAAGCATGAGATGGATTTTGATGCTGAATGGCTATTTGAAAATCATGAT
       F  N  M  K  E  L  N  K  V  K  H  E  M  D  F  D  A  E  W  L  F  E  N  H  D    850
2551  GAGAAGGATTCCAGAGTTAATTGGAAGAATCAATGCTAGTAAGACTGCTGACAAAAAGCTCAACCTTGGGAAGGAAGATGACAGTTCC
       E  K  D  S  R  V  N  A  S  K  T  A  D  K  K  L  N  L  G  K  E  D  D  S  S    875
2626  TCAGACAGTTTGAAAATCTCTAACGATAACCCAGATAACCCAGAAGGTAATTCCTGAAGGTGCTTCAGAATCTGAGGAG
       S  D  S  F  E  N  L  E  E  S  N  E  S  G  S  P  F  D  P  V  F  E  V  E    900
2701  CCTAAAATCTCTAACGATAACCCAGAAGAACATGTACTGAAGGTAATTCCTGAAGATGCTTCAGAATCTGAGGAG
       P  K  I  S  N' D  N  P  E  E  H  V  L  K  V  I  P  E  D  A  S  E  S  E  E    925
2776  AAGCTAGACCAAAAGAGAGGATGGTTCAAAATACGAAACTATTCATTGACTGGAAAGACGGTGCTTCCATCTGAGACTGCAC
       K  L  D  Q  K  E  D  G  S  K  Y  E  T  I  H  H  L  T  E  E  P  T  K  L  M  H    950
2851  AATGCATCTGATAGTGAGGTTGACCAAGACGATGTTGTTGAGTGGAAAGACGGTGCTTCCATCTGAGAGTGGG
       N  A  S  D  S  E  V  D  Q  D  D  V  V  E  W  K  D  G  A  S  P  S  E  S  G    975
2926  CCTGGATCCCAACAAGTGTCAGACTTTGAGGACAATACCTGCGAAATGAAACCAGGAACCTGGTCTGACGAGTCT
       P  G  S  Q  Q  V  S  D  F  E  D  N  T  C  E  M  K  P  G  T  W  S  D  E  S   1000
```

| Base # | Polymorphism | Sequences found in comparison to H7: |
|---|---|---|
| 2076 | G/A | H7/ref.7 |
| 2568 | C/T | H7/ref.7 |
| 3327 | A/G | H7/H3, ref.7Contig-dJ914P20.02099. Of the eight hADNP clones 50% had G and 50% A. |
| 3359 | C/A | H7/contig- dJ914P20.02099 |

FIG. 6

METHODS OF INHIBITING CANCER CELLS WITH ADNF III ANTISENSE OLIGONUCLEOTIDES

CROSS-REFERENCES TO RELATED APPLICATIONS

This application is related to U.S. Ser. No. 07/871,973, filed Apr. 22, 1992, now U.S. Pat. No. 5,767,240; U.S. Ser. No. 08/342,297, filed Oct. 17, 1994 (published as WO96/11948); U.S. Ser. No. 60/037,404, filed Feb. 7, 1997; PCT/US98/02485, filed Feb. 6, 1998 (published as WO98/35042); U.S. Ser. No. 09/187,330, filed Nov. 11, 1998; and U.S. Ser. No. 09/267,511, filed Mar. 12, 1999. All of these applications are incorporated herein by reference.

BACKGROUND OF THE INVENTION

Chromosome abnormalities such as deletions, multiplication of chromosomal segments and gene amplifications are often associated with cancers. The amplification and deletion of DNA sequences containing proto-oncogenes and tumor suppressor genes are characteristic of tumorigenesis. In breast tumors, for example, comparative genomic hybridization has revealed approximately 20 regions of recurrent increased DNA copy number (Kallioniemi et al., 1994, *Proc. Natl. Acad. Sci. USA*, 91:2156–60; Isola et al., 1995, *Am. J. Path.*, 147: 905–11). These regions are predicted to encode dominantly acting genes that may play a role in tumor progression or response to therapy. Three of these regions have been associated with oncogenes: ERBB2 at 17q12, MYC at 8q24, and CCND1 and EMSI at 1q13. Amplification at 20q13, which occurs in a variety of tumor types, has not previously been associated with a known oncogene (Collins at al., 1998, *Proc. Natl. Acad. Sci. USA*, 95: 8703–08). The identification, cloning, and study of the genes involved in these chromosomal regions, e.g., 20q13, is crucial to the study of tumorigenesis and to the development of cancer diagnostics and therapeutics.

ADNF III is an activity dependent neurotrophic factor that has neurotrophic/neuroprotective activity as measured with in vitro cortical neuron culture assays described by, e.g., Hill et al., 1993, *Brain Res.* 603:222–233; Gozes et al., 1996, *Proc. Natl. Acad. Sci. USA* 93:427–432; Brenneman et al., 1988, *Nature* 335:636; Brenneman et al., 1990, *Dev. Brain Res.* 51:63; Forsythe & Westbrook, 1988, *J. Physiol. Lond.* 396:515. Previously, an ADNF III polypeptide has been shown to be involved in prevention of neuronal cell death (U.S. Ser. No. 60/037,404; PCT/US98/02485; U.S. Ser. No. 09/187,330) and ADNF III polypeptide have recently been shown to prevent conditions associated with fetal alcohol syndrome (U.S. Ser. No. 09/267,511). However, the ADNF III gene has not previously been shown to be involved in tumorigenesis, and has not been used to inhibit cancer cell growth.

SUMMARY OF THE INVENTION

It has been discovered that the ADNF III gene is unexpectedly located in a chromosomal region associated with cancer. Surprisingly, it has been found that ADNF III antisense oligonucleotides inhibit the growth of pathologically proliferating cells such as cancer cells. The present invention therefore provides methods and kits for inhibiting the proliferation of pathologically proliferating cells by using human ADNF III antisense oligonucleotides. The invention further provides methods and kits for detecting altered regulation of ADNF III in human cancers.

The methods and kits for inhibiting pathologically proliferating cells comprise the step of contacting the cells with an antisense oligonucleotide that is substantially complementary, preferably fully complementary, to a subsequence of an ADNF III nucleic acid. The ADNF III nucleic acid is preferably a human ADNF III nucleic acid, and preferably an ADNF III mRNA. The methods may also comprise the step of contacting the cells with two or more antisense oligonucleotides that are complementary to two or more different subsequences of an ADNF III nucleic acid. In one embodiment, the oligonucleotides used in these methods and kits are substantially complementary to a subsequence of the 5' region of the ADNF III mRNA, and are preferably complementary to a subsequence of the ADNF III mRNA that encodes a methionine. In one embodiment, the oligonucleotides used in these methods are added to the pathologically proliferating cells at a concentration of 10 $\mu$M.

The methods for detecting pathologically proliferating cells comprise the steps of comparing the level of ADNF III expression in a test cell with the level of ADNF III expression in a control cell, as determined by contacting the cells with a nucleic acid probe that is substantially complementary, preferably fully complementary, to a subsequence of an ADNF III mRNA, and identifying as a pathologically proliferating cell a cell in which ADNF III mRNA expression is at least twice the level of ADNF III mRNA expression in the control normal cell. The nucleic acid probes used in these methods preferably comprise a detectable moiety.

These methods and kits for inhibiting and detecting pathologically proliferating cells can be used to inhibit and/or detect the growth of malignant pathologically proliferating cells, such as breast cancer, neuroblastoma, ovarian cancer, endometrial cancer, prostate cancer, bladder cancer, lung cancer, esophageal cancer, neuroendocrine cancer, brain cancer, colon cancer, testicular cancer, pancreatic cancer, and leukemia cancer cells. These methods and kits can also be used to inhibit and/or detect the growth of benign pathologically proliferating cells such as restenotic plaques in vascular smooth muscle (atherosclerosis and restenosis), benign prostatic hyperplasia cells, retinal hemangioblastomas, and psoriatic cells.

The invention also provides kits for inhibiting and detecting pathologically proliferating cells comprising nucleic acid probes that are substantially complementary to a subsequence of an ADNF III mRNA, preferably fully complementary to a subsequence of the ADNF III mRNA. The nucleic acid probes used in these kits preferably comprise a detectable moiety.

In one embodiment, the oligonucleotides and nucleic acid probes used in the methods and kits of the invention are selected from the group consisting of:
5'-TTGACAGGAAGTTGGAACAT-3' (SEQ ID NO:1),
5'-GCTTCATAGGACTTTGGCAT-3' (SEQ ID NO:2),
5'-ATCCTTGGTGGGAGTCCCAT-3' (SEQ ID NO:3), and
5'-ACCTAGACCCAGTCTCAT-3' (SEQ ID NO:6).

Preferably, the oligonucleotides and probes are fully complementary to an ADNF III mRNA, preferably to a human ADNF III mRNA. In one embodiment, the oligonucleotides are complementary to the 5' region of the ADNF nucleic acid.

The antisense oligonucleotides of the invention may be ribozymes.

Additionally, the oligonucleotides and nucleic acid probes of the invention may be DNA oligonucleotides, peptide nucleic acid oligonucleotides, phosphorothioate oligonucleotides, or 2'-O methyl oligonucleotides. The oligonucleotides and probes are from about 8 to 50 nucleotides in length, and preferably about 15 to 25 nucleotides in length.

BRIEF DESCRIPTION OF THE DRAWINGS

Figure 4:
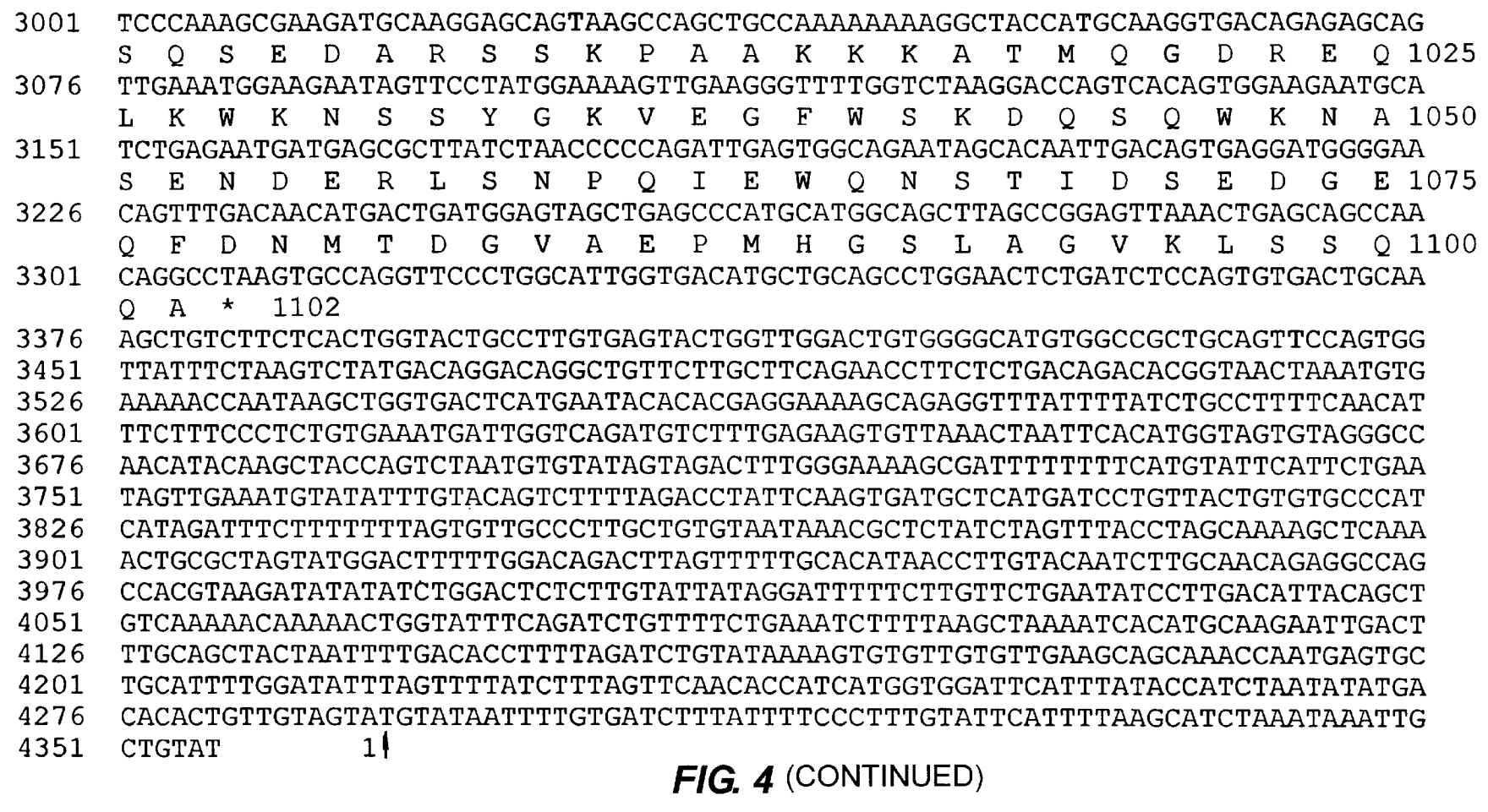

FIG. 4 shows the sequence of the hADNF III gene (SEQ ID NO:7) and encoded amino acid sequence (SEQ ID NO:8) and indicates the location of the antisense oligodeoxynucleotides selected for use in cancer cell growth inhibition experiments. Regions complementary to the antisense oligodeoxynucleotide areas are bold, underlined, and indicated by numbers 1, 8, 9, 7, 67, and 68.

FIG. 6 shows polymorphic sites in human ADNF III.

DETAILED DESCRIPTION OF THE PRESENT INVENTION AND PREFERRED EMBODIMENTS

I. Introduction: General Overview

Figure 1:
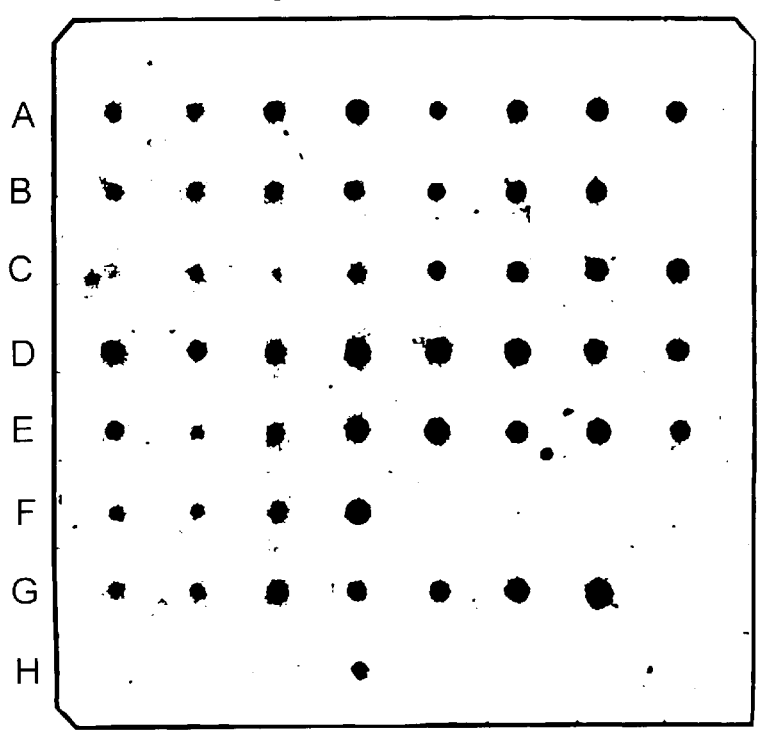
FIG. 1 presents patterns of expression of the human ADNF III mRNA. The human ADNF III mRNA is expressed in multiple tissues, with increases in embryonic tissues, glandular tissues and brain tissues.
Figure 2:
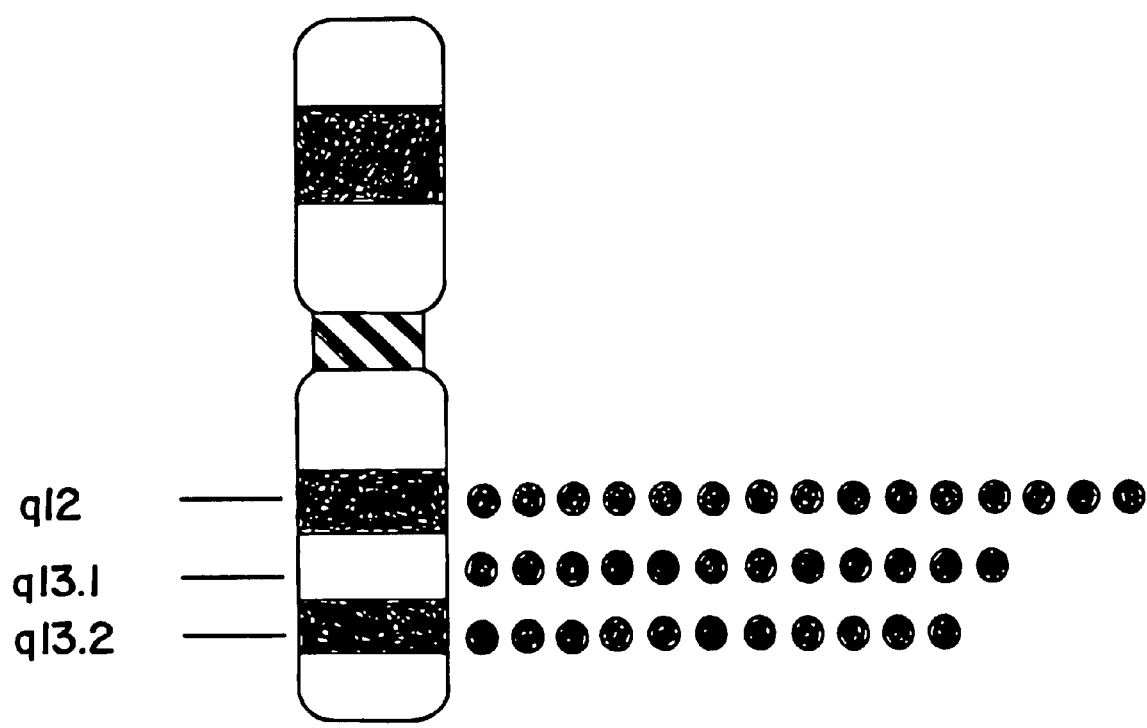
FIG. 2 presents the chromosomal localization of the human ADNF III gene. The diagram shows the hybridization sites of the hADNF III gene.

ADNF III has previously been shown to be involved in prevention of neuronal cell death (see, e.g., Bassan et al., 1999, *J. Neurochem.* 72:1283–93), and in prevention of a condition associated with fetal alcohol syndrome (U.S. Ser. No. 09/267,511). However, the ADNF III gene has not previously been shown to be associated with cancer, and has not been used to inhibit cancer cell growth.

It has now been discovered that antisense oligonucleotides complementary to the human ADNF III mRNA are effective for inhibiting the proliferation of cancer cells. For instance, proliferation of HT-29 colon cancer cells contacted with antisense oligonucleotides complementary to subsequences of the 5' region of the ADNF III MRNA was inhibited by 90%. In addition, the hADNF III gene was found to be localized to chromosome 20q12–13, a region frequently amplified in a variety of tumor types. In fact, expression of ADNF III mRNA was found to be increased in human breast cancer cells approximately 14 times as compared to control. In addition, ADNF III mRNA expression in colon cancer cells was increased approximately 2.5 to 3.5-fold over control.

The present invention thus provides methods of using ADNF III oligonucleotides to inhibit the growth of pathologically proliferating cells. The invention further provides methods and kits to detect the presence of pathologically proliferating cells in human tissues. The methods of the invention find use in therapeutic applications to reduce the proliferation of cancer cells, such as breast, neuroblastoma, ovarian, endometrial, prostate, bladder, lung, esophageal, neuroendocrine, leukemia, brain, colon, testicular, and pancreatic cancer cells. in addition to other pathologically proliferating cancer cells. The methods and kits of the invention are of further use and value to detect cancers, such as breast cancer, neuroblastoma, ovarian cancer, endometrial cancer, prostate cancer, bladder cancer, lung cancer, esophageal cancer, neuroendocrine cancer, brain cancer, colon cancer, testicular cancer, pancreatic cancer, leukemia, and other conditions associated with pathologically proliferating cells, in which ADNF III expression is increased as compared to a control.

II. Definitions

The phrase "ADNF III" refers to an activity dependent neurotrophic factor (ADNF) having a predicted molecular weight of about 123 kDa (about 1102 amino acid residues) and a pI of about 6.97. ADNF III is also referred to as ADNP for "activity dependent neuroprotective factor." An "ADNF III polypeptide" refers to an ADNF polypeptide having an active site comprising the amino acid sequence NAPVSIPQ (see, Bassan et al., 1999, *J. Neurochem.* 72:1283–1293, incorporated herein by reference), and any conservatively modified variants thereof that have neurotrophic/neuroprotective activity as measured with in vitro cortical neuron culture assays described by, e.g., Hill et al., 1993, *Brain Res.* 603, 222–233; Gozes et al., 1996, *Proc. Natl. Acad. Sci. USA* 93:424–432; Brenneman et al., 1988, *Nature* 335:636; Brenneman et al., 1990, *Dev. Brain Res.* 51:63; Forsythe & Westbrook, 1988, *J. Physiol. Lond.* 396:515. An ADNF III polypeptide can be an ADNF III polypeptide, an allele, polymorphic variant, interspecies homolog, or any subsequence thereof that exhibits neuroprotective/neurotrophic action on, e.g., neurons originating in the central nervous system either in vitro or in vivo. An "ADNF III RNA" is an RNA, particularly an mRNA, that encodes an ADNF III polypeptide described herein, and any conservatively modified variants thereof.

The terms "polypeptide," "peptide," and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers.

The term "amino acid" refers to naturally occurring amino acids, amino acid analogs, and amino acid mimetics that function in a manner similar to the naturally occurring and analog amino acids. Naturally occurring amino acids are those encoded by the genetic code, as well as those amino acids that are later modified, e.g., hydroxyproline, γ-carboxyglutamate, and O-phosphoserine. Amino acid analogs refer to synthetic amino acids that have the same basic chemical structure as a naturally occurring amino acid, i.e., an α carbon that is bound to a hydrogen, a carboxyl group, an amino group, and an R group (e.g., homoserine, norleucine, methionine sulfoxide, methionine methyl sulfonium). Such analogs have modified R groups (e.g., norleucine) or modified peptide backbones, but retain the same basic chemical structure as a naturally occurring amino acid. Both naturally occurring and analog amino acids can be made synthetically. Amino acid mimetics refer to chemical compounds that have a structure that is different from the general chemical structure of an amino acid, but that function in a manner similar to a naturally occurring amino acid.

"Conservatively modified variants" applies to both amino acid and nucleic acid sequences. With respect to particular nucleic acid sequences, conservatively modified variants refer to those nucleic acids which encode identical or essentially identical amino acid sequences, or where the nucleic acid does not encode an amino acid sequence, to essentially identical sequences. Specifically, degenerate codon substitutions may be achieved by generating sequences in which the third position of one or more selected (or all) codons is substituted with mixed-base and/or deoxyinosine residues (Batzer et al., 1991, *Nucleic Acid Res.* 19:5081; Ohtsuka et al., 1985, *J. Biol. Chem.* 260:2605–2608; Rossolini et al., 1994, *Mol. Cell. Probes* 8:91–98). Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following groups each contain amino acids that are conservative substitutions for one another:
1) Alanine (A), Glycine (G);
2) Serine (S), Threonine (T);
3) Aspartic acid (D), Glutamic acid (E);
4) Asparagine (N), Glutamine (Q);
5) Cysteine (C), Methionine (M);
6) Arginine (R), Lysine (K), Histidine (H);
7) Isoleucine (I), Leucine (L), Valine (V); and
8) Phenylalanine (F), Tyrosine (Y), Tryptophan (W).
(see, e.g., Creighton, 1984, *Proteins*).

As used herein, the phrase "inhibiting the growth" refers to reducing, including preventing, cell division. Reduction is a change of a parameter by about 10% to about 100%, preferably at least about 25%, and more preferably at least about 50 or 90% compared to that of the control (e.g., without treatment with, e.g., antisense ADNF III oligonucleotides). The inhibition of growth can be measured by any methods known in the art. For example, viable cell number in treated, inhibited samples can be compared with viable cell number in control samples, determined by a 3 hour incubation with the MTS reagent (CellTiter 96 AQ$_{ucous}$ cell proliferation kit, Promega, Madison, Wis., USA). The MTS reagent is oxidized by active mitochondria, resulting in increases in light absorbance at 490 nm (evaluated by a multiscan plate reader) (see, Example IV). In addition, growth inhibition can be measured by assays that can detect reductions in cell proliferation in vitro or in vivo, such as $^3$H incorporation assays, changes in ability to form foci, anchorage dependence, decreased semi-solid or soft agar growth, changes in contact inhibition and density limitation of growth, changes in growth factor or serum requirements, changes in cell morphology, losing immortalization, losing tumor specific markers, and/or inability to form or suppress tumors when injected into animal hosts. See generally, Freshney, 1994, *Culture of Animal Cells a Manual of Basic Technique*, 3$^{rd}$ ed., Wiley-Liss, Inc., pp.231–241, herein incorporated by reference.

The term "pathologically proliferating cell" is intended to include, but is not limited to, cells having the capacity for autonomous growth, i.e., existing and reproducing independently of normal regulatory mechanisms. These cells are pathologic because they deviate from normal cells as a result of a disease state, disorder, infection, or otherwise abnormal condition. Pathologically proliferating cells are benign hyperproliferating cells (such as restenotic plaques in vascular smooth muscle, benign prostatic hyperplasia cells, retinal hemangioblastomas, and psoriatic cells) or malignant hyperproliferating cells (such as cancer cells characteristic of cancers such as osteosarcoma, fibrosarcoma, glioblastoma, breast cancer, colon cancer, lung cancer, transitional cell carcinoma of the bladder, small cell lung carcinoma, non-small cell lung carcinoma, renal cell carcinoma, or neuroblastoma).

The occurrence of pathological proliferation can be established by assays for cell growth and proliferation characteristics in vitro or in vivo, such as $^3$H incorporation assays, formation of foci, anchorage independence, semi-solid or soft agar growth, changes in contact inhibition and density limitation of growth, loss of growth factor or serum requirements, changes in cell morphology, gaining or losing immortalization, gaining or losing tumor specific markers, ability to form or suppress tumors when injected into suitable animal hosts, and/or immortalization of the cell. See, e.g., Freshney, 1994, *Culture of Animal Cells a Manual of Basic Technique*, 3$^{rd}$ ed., Wiley-Liss, Inc., pp.231–241, herein incorporated by reference.

A "cancer cell" refers to a cell exhibiting phenotypic changes, such as immortalization, aberrant growth control, and/or malignancy, as a result of genetic transformation. Transformation may arise following exposure to a carcinogen, thereby mutating an endogenous gene; from infection with a transforming virus and incorporation of new genomic DNA; from uptake of exogenous DNA; or spontaneously. The term also encompasses pre-cancerous cells, having a genetic alteration that predisposes them to malignant transformation (see, Freshney, 1994, *Culture of Animal Cells a Manual of Basic Technique*, 3$^{rd}$ ed., Wiley-Liss, Inc.).

The term "contacting" is used herein interchangeably with the following: combined with, added to, mixed with, passed over, incubated with, flowed over, etc. Moreover, the ADNF III nucleic acid probes and antisense oligonucleotides of the present invention can be "administered" by any conventional method such as, for example, parenteral, oral, topical, and inhalation routes.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

As used herein "oligonucleotide" or, alternatively, "polynucleotide" refer to a nucleic acid sequence of approximately 8 nucleotides or greater in length, and up to as many as approximately 100 nucleotides in length, which can be used as a primer, probe or amplimer. Preferably, oligonucleotides are between about 10 and about 50 nucleotides in length, more preferably between about 15 and about 25 nucleotides, and even more preferably, between about 20 and about 30 nucleotides. The terms oligonucleotides, polynucleotides, or oligomers also refer to synthetic and/or non-naturally occurring nucleic acids (i.e., comprising nucleic acid analogues or modified backbone residues or linkages).

An "antisense" oligonucleotide is a polynucleotide that is substantially or fully complementary to a target ADNF III polynucleotide and has the ability to specifically hybridize to the target ADNF III polynucleotide.

A "ribozyme" is a molecule of RNA that has catalytic activity. The ribozymes of the invention are antisense oligonucleotides that bind and enzymatically cleave and inactivate ADNF III RNA. Useful ribozymes can comprise 5'- and 3'-terminal sequences complementary to the ADNF III RNA and can be engineered by one of skill on the basis of the ADNF III RNA sequence. Ribozymes of the invention include those having characteristics of group I intron ribozymes (Cech, 1995, *Biotechnology* 13:323) and others of hammerhead ribozymes (Edgington, 1992, *Biotechnology* 10:256).

The term "substantially complementary" refers to a nucleic acid segment that will hybridize, under stringent hybridization conditions, to a complement of another nucleic acid strand. As is known to one of skill in the art, stringent hybridization conditions can be adjusted within the designated range to allow for higher or lower percent mismatches between a probe and its target.

The term "fully complementary" refers to a nucleic acid that has no mismatches when hybridized to its complementary nucleic acid strand, e.g., the complement of the complement has 100% identity with the target nucleic acid subsequence. A perfectly complementary probe is also substantially complementary.

"Subsequence" refers to a sequence of nucleic acids which comprise a part of a longer sequence of nucleic acids.

The "5' region" of a gene or RNA refers to the portion of the gene or RNA encoding the amino terminus of the gene product.

The phrase "encoding a methionine" refers to the portion of the ADNF III RNA containing putative start sites of translation at a methionine residue.

A "synthetic" oligonucleotide refers to a polynucleotide synthesized using in vitro chemical methods, e.g., by using a machine that synthesizes polynucleotides using the phosphodiester method, the diethylphosphoramidite method, the phosphotriester methods, the solid support method, and other methods known to those skilled in the art.

As used herein, "recombinant" refers to a polynucleotide enzymatically synthesized or otherwise manipulated in vitro or in vivo (e.g., "recombinant polynucleotide"); to methods of using recombinant polynucleotides to produce gene products in cells or other biological systems; or to a polypeptide ("recombinant protein") encoded by a recombinant polynucleotide. When used with reference to, e.g., a cell, the term "recombinant" also indicates that the cell has been modified by the introduction of a heterologous nucleic acid or protein or the alteration of a native nucleic acid or protein (e.g., cloning a gene into an expression vector), or that the cell is derived from a cell so modified. Thus, for example, recombinant cells express genes that are not found within the native (non-recombinant) form of the cell or express native genes that are otherwise abnormally expressed, under expressed or not expressed at all.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

A "constitutive" promoter is a promoter that is active under most environmental and developmental conditions. An "inducible" promoter is a promoter that is active under environmental or developmental regulation.

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The term "transfect" or "transduce" refers to any way of getting a nucleic acid across a cell membrane, including electroporation, biolistics, injection, plasmid transfection, lipofection, viral transduction, lipid-nucleic acid complexes, naked DNA, etc.

A "host cell" is a naturally occurring cell or a transformed cell that contains an expression vector and supports the replication or expression of the expression vector. Host cells may be cultured cells, explants, cells in vivo, and the like. Host cells may be prokaryotic cells such as *E. coli,* or eukaryotic cells such as yeast, insect, amphibian, or mammalian cells such as CHO, HeLa, HCT116, RK0, HT-29 cells, and the like.

The terms "isolated," "purified," or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated ADNF III nucleic acid is separated from open reading frames that flank the ADNF III gene and encode proteins other than ADNF III. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The terms "identical" or percent "identity," in the context of two or more nucleic acids or polypeptide sequences, refer to two or more sequences or subsequences that are the same or have a specified percentage of amino acid residues or nucleotides (i.e., 70% identity) that are the same, when compared and aligned for maximum correspondence over a comparison window, as measured using a sequence comparison algorithm or by manual alignment and visual inspection. Such sequences are then said to be "substantially identical." This definition also refers to the complement of a test sequence. Preferably, the percent identity exists over a region of the sequence that is at least about 25 amino acids in length, more preferably over a region that is 50 or 100 amino acids in length.

For sequence comparison, one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, 1981, *Adv. Appl. Math.* 2:482, by the homology alignment algorithm of Needleman & Wunsch, 1970, *J. Mol. Biol.* 48:443, by the search for similarity method of Pearson & Lipman, 1988, *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

The phrase "selectively (or specifically) hybridizes to" refers to the binding, duplexing, or hybridizing of a molecule only to a particular nucleic acid sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, 1993, "Overview of principles of hybridization and the strategy of nucleic acid assays," in *Techniques in Biochemistry and Molecular Biology—Hybridization with Nucleic Probes.* Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with a wash in 0.2×SSC, and 0.1% SDS at 65° C.

"Nucleic acid probe" or "probe" refers to an oligonucleotide that binds through complementary base pairing to a subsequence of a target nucleic acid. The nucleic acid probe may be, for example, a DNA fragment prepared by amplification methods such as by PCR or, it may be synthesized by either the phosphoramidite method described by Beaucage and Carruthers, 1981, *Tetrahedron Lett.,* 22:1859–1862, or by the triester method according to Matteucci, et al. 1981, *J. Am. Chem. Soc.,* 103:3185, both of which are incorporated herein by reference. By assaying for the presence or absence of the probe, one can detect the presence or absence of the select sequence or subsequence.

A "labeled nucleic acid probe or oligonucleotide" is one that is bound, either covalently, through a linker or a chemical bond, or noncovalently, through ionic, van der Waals, electrostatic, or hydrogen bonds, to a detectable moiety such that the presence of the probe may be detected by detecting the presence of the detectable moiety bound to the probe. Probes are optionally directly labeled with detectable moieties, for example, radioisotopes and fluorescent molecules, or indirectly labeled with, for example, biotin or digoxigenin which are used in conjunction with their labeled, naturally occurring anti-ligands.

A "detectable moiety" is a composition detectable by spectroscopic, photochemical, biochemical, immunochemical, or chemical means. For example, useful detectable moieties or labels include, but are not limited to, $^{32}P$, fluorescent dyes, electron-dense reagents, enzymes (e.g., as commonly used in an ELISA), biotin, digoxigenin, or haptens and proteins for which antisera or monoclonal antibodies are available.

III. Methods and Kits

A. Methods for Inhibiting the Growth of Cancer Cells

It has surprisingly been discovered that the administration of an hADNF III antisense oligonucleotide to human cancer cells results in inhibition of cell division. The invention thus provides, inter alia, methods of using ADNF III antisense oligonucleotides to inhibit the growth of pathologically proliferating cells, such as cancer cells.

The methods provided for using ADNF III antisense oligonucleotides to inhibit the growth of hyperproliferating cells (e.g., cancer cells) comprise contacting the hyperproliferating cells with an antisense oligonucleotide that is substantially complementary to a subsequence of the ADNF III mRNA.

In one embodiment, the hyperproliferating cells are contacted with the antisense oligonucleotides at a concentration of about 5 $\mu$M to about 50 $\mu$M, preferably about 10 $\mu$M.

In one embodiment, the preferred antisense oligonucleotides are characterized as being complementary to subsequences of the 5' region of the ADNF III mRNA. The preferred antisense oligonucleotides are further characterized as being complementary to subsequences of ADNF III that encode a methionine, or a putative start site of translation, close to the transcription initiation site. Preferred antisense oligonucleotides are typically at least 8 nucleotides in length and may be typically up to about 100 nucleotides in length, preferably between 15 and 25 nucleotides in length. Exemplary ADNF III antisense oligonucleotides of present invention include:

5'-TTGACAGGAAGTTGGAACAT-3' (SEQ ID NO:1) (1, in FIG. 4);

5'-GCTTCATAGGACTTTGGCAT-3' (SEQ ID NO:2) (8, in FIG. 4);

5'-ATCCTTGGTGGGAGTCCCAT-3' (SEQ ID NO:3) (9, in FIG. 4);

5'-ACCTAGACCCAGTCTCAT-3' (SEQ ID NO:6) (68, in FIG. 4).

Other ADNF III antisense oligonucleotides that are effective in inhibiting the growth of pathologically proliferating cells can be identified using the screening methods of the present invention, e.g., by contacting target cancer cells with the ADNF III antisense polynucleotides to be screened and determining whether the growth of the cancer cells is inhibited (see, Definitions, supra, for a description of assays used to detect reductions in cell proliferation). The ADNF III antisense polynucleotides of present invention can be antisense oligodeoxynucleotides, ribozymes, or triplex compositions that inhibit ADNF III expression and activity. The antisense polynucleotides can be deoxyribonucleotides, ribonucleotides, or polynucleotides containing nucleotide analogs, such as phosphorothioates, phosphoramidates, methyl phosphonates, chiral-methyl phosphonates, 2-O-methyl ribonucleotides, or peptide-nucleic acids (PNAs).

In one embodiment, the ADNF III antisense oligonucleotides are fully complementary to the human ADNF III mRNA. The antisense oligonucleotides may also be fully or substantially complementary to the ADNF III mRNA from human, mouse, or other mammals.

In another embodiment, the target cancer cells are human cancer cells. In a preferred embodiment, the hADNF III antisense oligonucleotides inhibit human cancer cell growth by at least 10%. More preferably, the hADNF III antisense oligonucleotides inhibit human cancer cell growth by about 50%. Most preferably, the hADNF III antisense oligonucleotides inhibit human cancer cell growth by greater than 90% (See, Example IV).

The method of the invention can be used to inhibit the growth of cancer cells ex vivo or in vivo. The method of the invention is particularly useful for inhibiting the growth of pathologically proliferating human cells ex vivo, including, but not limited to, human cancer cells, such as leukemia, breast cancer, neuroblastoma, ovarian cancer, endometrial cancer, prostate cancer, bladder cancer, lung cancer, esophageal cancer, neuroendocrine cancer, brain cancer, colon cancer, testicular cancer, and pancreatic cancer cells. It is further contemplated that the methods of the invention will find use in therapeutic applications for conditions and diseases associated with the pathological proliferation of cells. Diseases that would benefit from the therapeutic applications of this invention include all diseases characterized by cell hyperproliferation including, for example, solid tumors and leukemias, and non-cancer conditions, such as retinal hemangioblastomatosis, postangioplasty vascular restenosis, benign prostate hyperplasia, atherosclerosis, psoriasis, and endometriosis.

B. Methods for Diagnosis of Pathologically Proliferating Cells

It has further been discovered that nucleic acid probes directed against ADNF III can be used to detect increases in ADNF III mRNA levels in tissues undergoing rapid proliferation, such as in immune cells, glandular tissues, fetal lung and liver, and in primary cancer tissues, including human breast and colon cancer tissues. Thus, the present invention provides methods of using nucleic acid probes that are complementary to a subsequence of an ADNF III mRNA (e.g., hADNF III nucleic acid probes) to detect and identify pathologically proliferating cells, including cancer cells.

The method provided herein for identifying a pathologically proliferating cell comprises using a nucleic acid probe directed against an ADNF III mRNA to compare the level of expression of ADNF III mRNA in a test cell with the level of expression of ADNF III mRNA in a control cell. A test cell is identified as a pathologically proliferating cell when the level of ADNF III expression is at least twice the level of ADNF III expression in the control cell, preferably at least 10 times the level in the control cell.

In one embodiment, the nucleic acid probe used in the method of the present invention is preferably fully complementary to a human ADNF III mRNA and the test cell is a human cell. The nucleic acid probe used in the method of the invention may also be fully or substantially complementary to an ADNF III mRNA of human, mouse, or another mammal. It will be apparent to one of skill that substitutions may be made in the nucleic acid probe which will not affect the ability of the probe to effectively detect the increased levels of ADNF III RNA in pathologically proliferating cells (e.g., cancer cells) and thus, such substitutions are within the scope of the present invention.

The nucleic acid probe used in the method of the present invention can be a DNA probe, a riboprobe, a peptide nucleic acid probe, a phosphorothioate probe, or a 2'-O methyl probe. The length of the nucleic acid probe may be from about 8 to 50 nucleotides, preferably from about 15 to 25 nucleotides in length. The method of the invention can be readily performed in a cell extract, cultured cell, or tissue sample from a human, a mammal, or other vertebrate.

As such, the methods of the present invention are useful for detecting the presence of increased ADNF III expression in vitro. Additionally, the methods of the invention are useful for detecting the presence of pathologically proliferating cells in cell cultures, and in human tissues, such as solid tumors and blood. Still further, these methods are useful for diagnostic applications, including diagnosing conditions characterized by pathological cell hyperproliferation, such as retinal hemangioblastomatosis, postangioplasty vascular restenosis, benign prostate hyperplasia, atherosclerosis, and psoriasis. The invention further contemplates the use of ADNF III as an important cancer marker, one whose levels can identify, detect and/or diagnose the presence of the cancerous state in human cancers cells, such as breast cancer cells, colon cancer cells, and neuroblastomas. The methods of the invention can also be used as a screening method that aids in diagnosing the presence of a cancerous tumor in a patient, the method comprising determining the presence and level of expression of hADNF III in tissue from the patient, the presence of increased hADNF III expression being indicative of cancer cells or pathological cell proliferation in the patient.

C. Kits

This invention also provides kits for detecting a pathologically proliferating cell, the kit comprising a nucleic acid probe that is substantially complementary to a subsequence of an ADNF III mRNA. The invention further provides kits for inhibiting the proliferation of pathologically proliferating cells, the kit comprising the step of contacting the cells with an antisense oligonucleotide that is substantially complementary, preferably fully complementary, to a subsequence of an ADNF III nucleic acid.

The kits can include a container containing one or more of the above-discussed nucleic acid probes or antisense oligonucleotides, with or without labels as discussed herein below. Also included in the kits can be a suitable membrane for separation and hybridization of sample RNA, preferably in the form of an assay apparatus that is adapted to use with the claimed methods. Preferably, the kits will also include reagents useful for detecting the presence of the detectable labels. Other materials useful in the performance of the assays can also be included in the kits, including RNA extraction buffers, hybridization buffers, test tubes, transfer pipettes, and the like. The kits can also include written instructions for carrying out the methods of the present invention.

The kits of the invention can also include an internal and/or an external control. An internal control can consist of an ADNF III polynucleotide. The control ADNF III polynucleotide can conveniently be preattached to a membrane to which the test sample is applied. The external control can also consist of an ADNF III polynucleotide. Typically, the ADNF III polynucleotide present in the external control will be at a concentration at or above the sensitivity limit of the assay. The external control ADNF III polynucleotide can be diluted in the sample diluent and assayed in the same manner as a biological sample. Alternatively, the external control ADNF III polynucleotide can be added to an aliquot of an actual biological sample to determine the sensitivity of the assay. The kits of the present invention can also contain materials sufficient for one detection assay, or can contain materials sufficient for multiple detection assays.

IV. How to Make ADNF III Antisense Oligonucleotides

As described herein, the present invention provides methods for using antisense polynucleotides, which have the ability to specifically hybridize to ADNF III. Without intending to be limited to any particular mechanism, it is believed that such antisense oligonucleotides bind to, and interfere with the translation of, the sense ADNF III mRNA. Alternatively, the antisense molecule may render the ADNF III mRNA susceptible to nuclease digestion, interfere with transcription, interfere with processing, localization or otherwise with RNA precursors ("pre-mRNA"), repress transcription of mRNA from the ADNF III gene, or act through some other mechanism. However, the particular mechanism by which the antisense molecule reduces ADNF III expression is not critical.

Generally, to assure specific hybridization, the antisense sequence is substantially complementary to the target ADNF III mRNA sequence. In certain embodiments, the antisense sequence is exactly complementary to the target sequence. The antisense polynucleotides may also include, however, nucleotide substitutions, additions, deletions, transitions, transpositions, or modifications, or other nucleic acid sequences or non-nucleic acid moieties so long as specific binding to the relevant target sequence corresponding to ADNF III RNA or its gene is retained as a functional property of the polynucleotide.

In one embodiment, the antisense sequence is complementary to relatively accessible sequences of the ADNF III mRNA (e.g., relatively devoid of secondary structure). These sequences can be determined by analyzing predicted RNA secondary structures using, for example, the MFOLD program (Genetics Computer Group, Madison Wis.) and testing in vitro or in vivo as is known in the art. Another useful method for identifying effective antisense compositions uses combinatorial arrays of oligonucleotides (see, e.g., Milner et al., 1997, *Nature Biotechnology* 15:537).

A. Triplex-forming Antisense Polynucleotides

As one embodiment of the antisense molecules described herein, the present invention provides polynucleotides that bind to double-stranded or duplex ADNF III nucleic acids (e.g., in a folded region of the ADNF III RNA or in the ADNF III gene), forming a triple helix-containing, or "triplex" nucleic acid. Triple helix formation results in inhibition of ADNF III expression by, for example, preventing transcription of the ADNF III gene, thereby reducing or eliminating ADNF III activity in a cell. Without intending to be bound by any particular mechanism, it is believed that triple helix pairing compromises the ability of the double helix to open sufficiently for the binding of polymerases, transcription factors, or regulatory molecules to occur.

Triplex oligo- and polynucleotides of the invention are constructed using the base-pairing rules of triple helix formation (see, e.g., Cheng et al., 1988, *J. Biol. Chem.* 263:15110; Ferrin and Camerini-Otero, 1991, *Science* 354:1494; Ramdas et al., 1989, *J. Biol. Chem.* 264:17395; Strobel et al., 1991, *Science* 254:1639; and Rigas et al., 1986, *Proc. Natl. Acad. Sci. U.S.A.* 83:9591; each of which is incorporated herein by reference) and the ADNF III mRNA and/or gene sequence. Typically, the triplex-forming oligonucleotides of the invention comprise a specific sequence of from about 10 to at least about 25 nucleotides or longer "complementary" to a specific sequence in the ADNF III RNA or gene (i.e., large enough to form a stable triple helix, but small enough, depending on the mode of delivery, to administer in vivo, if desired). In this context, "complementary" means able to form a stable triple helix. In one embodiment, oligonucleotides are designed to bind specifically to the regulatory regions of the ADNF III gene (e.g., the ADNF III 5'-flanking sequence, promoters, and enhancers) or to the transcription initiation site (e.g., between −10 and +10 from the transcription initiation site or translation start site, e.g., at a methionine residue). For a review of recent therapeutic advances using triplex DNA, see Gee et al., in Huber and Carr, 1994, *Molecular and Immunologic Approaches*, Futura Publishing Co, Mt Kisco, N.Y. and Rininsland et al., 1997, *Proc. Natl. Acad. Sci. USA* 94:5854, which are both incorporated herein by reference.

B. Ribozymes

In another embodiment, the present invention provides ribozymes useful for inhibiting ADNF III activity. The ribozymes of the invention bind and enzymatically cleave and inactivate ADNF III mRNA. Useful ribozymes can comprise 5'- and 3'-terminal sequences complementary to the ADNF III mRNA and can be engineered by one of skill on the basis of the ADNF III mRNA sequence. Ribozymes of the invention include those having characteristics of group I intron ribozymes (Cech, 1995, *Biotechnology* 13:323) and others of hammerhead ribozymes (Edgington, 1992, *Biotechnology* 10:256).

Ribozymes of the invention include those having cleavage sites, such as GUA, GUU and GUC. Other optimum cleavage sites for ribozyme-mediated inhibition of telomerase activity in accordance with the present invention include those described in PCT Publications WO 94/02595 and WO 93/23569, both incorporated herein by reference. Short RNA oligonucleotides between 15 and 20 ribonucleotides in length corresponding to the region of the target ADNF III gene containing the cleavage site can be evaluated for secondary structural features that may render the oligonucleotide more desirable. The suitability of cleavage sites may also be evaluated by testing accessibility to hybridization with complementary oligonucleotides using ribonuclease protection assays, or by testing for in vitro ribozyme activity in accordance with standard procedures known in the art.

As described by Hu et al., PCT Publication WO 94/03596, incorporated herein by reference, antisense and ribozyme functions can be combined in a single oligonucleotide. Moreover, ribozymes can comprise one or more modified nucleotides or modified linkages between nucleotides, as described above in conjunction with the description of illustrative antisense oligonucleotides of the invention.

C. Synthesis of Antisense Polynucleotides

The antisense nucleic acids (DNA, RNA, modified, analogues, and the like) can be made using any suitable method for producing a nucleic acid, such as the chemical synthesis and recombinant methods disclosed herein and known to one of skill in the art. In one embodiment, for example, antisense RNA molecules of the invention may be prepared by de novo chemical synthesis or by cloning. For example, an antisense RNA that hybridizes to ADNF III mRNA can be made by inserting (ligating) an ADNF III DNA sequence in reverse orientation operably linked to a promoter in a vector (e.g., plasmid). Provided that the promoter and, preferably termination and polyadenylation signals, are properly positioned, the strand of the inserted sequence corresponding to the noncoding strand will be transcribed and act as an antisense oligonucleotide of the invention.

The present invention also provides ADNF III antisense polynucleotides (RNA, DNA or modified) that can be produced by direct chemical synthesis. Chemical synthesis is generally preferred for the production of oligonucleotides or for oligonucleotides and polynucleotides containing nonstandard nucleotides (e.g., probes, primers and antisense oligonucleotides). Direct chemical synthesis of nucleic acids can be accomplished by methods known in the art, such as the phosphotriester method of Narang et al., 1979, *Meth. Enzymol.* 68:90; the phosphodiester method of Brown et al., 1979, *Meth. Enzymol.* 68:109; the diethylphosphoramidite method of Beaucage et al., 1981, *Tetra. Lett.*, 22:1859; and the solid support method of U.S. Pat. No. 4,458,066.

Chemical synthesis typically produces a single stranded oligonucleotide, which may be converted into double stranded DNA by hybridization with a complementary sequence, or by polymerization with a DNA polymerase and an oligonucleotide primer using the single strand as a template. One of skill will recognize that while chemical synthesis of DNA is often limited to sequences of about 100 or 150 bases, longer sequences may be obtained by the ligation of shorter sequences or by more elaborate synthetic methods.

It will be appreciated that the ADNF III oligonucleotides of the invention can be made using nonstandard bases (e.g., other than adenine, cytidine, guanine, thymine, and uridine) or nonstandard backbone structures to provides desirable properties (e.g., increased nuclease-resistance, tighter-binding, stability or a desired $T_m$). Techniques for rendering oligonucleotides nuclease-resistant include those described in PCT Publication WO 94/12633. A wide variety of useful modified oligonucleotides may be produced, including oligonucleotides having a peptide-nucleic acid (PNA) backbone (Nielsen et al., 1991, *Science* 254:1497) or incorporating 2'-O-methyl ribonucleotides, phosphorothioate nucleotides, methyl phosphonate nucleotides, phosphotriester nucleotides, phosphorothioate nucleotides, phosphoramidates. Still other useful oligonucleotides may contain alkyl and halogen-substituted sugar moieties comprising one of the following at the 2' position: OH, SH, $SCH_3$, F, OCN, $OCH_3OCH_3$, $OCH_3O(CH_2)_nCH_3$, $O(CH_2)_nNH_2$ or $O(CH_2)_nCH_3$, where n is from 1 to about 10; $C_1$ to $C_{10}$ lower alkyl, substituted lower alkyl, alkaryl or aralkyl; Cl; Br; CN; $CF_3$; $OCF_3$; O—, S, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a cholesteryl group; a folate group; a reporter group; an intercalator; a group for improving the pharnacokinetic properties of an oligonucleotide; or a group for improving the pharmacodynamic properties of an oligonucleotide and other substituents having similar properties. Folate, cholesterol or other groups that facilitate oligonucleotide uptake, such as lipid analogs, may be conjugated directly or via a linker at the 2' position of any nucleoside or at the 3' or 5'position of the 3'-terminal or 5'-terminal nucleoside, respectively. One or more such conjugates may be used. Oligonucleotides may also have sugar mimetics such as cyclobutyls in place of the pentofuranosyl group. Other embodiments may include at least one modified base form or "universal base" such as inosine, or inclusion of other nonstandard bases such as queosine and wybutosine as well as acetyl-, methyl-, thio- and similarly modified forms of adenine, cytidine, guanine, thymine, and uridine which are not as easily recognized by endogenous endonucleases.

The invention further provides oligonucleotides having backbone analogues, such as phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, chiral-methyl phosphonates, nucleotides with short chain alkyl or cycloalkyl intersugar linkages, short chain heteroatomic or heterocyclic intersugar ("backbone") linkages, or $CH_2$—NH—O—$CH_2$, $CH_2$—N($CH_3$)—$OCH_2$, $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—P—O—$CH_2$), or mixtures of the same. Also useful are oligonucleotides having morpholino backbone structures (U.S. Pat. No. 5,034,506).

Useful references include: F. Eckstein, ed., 1991, *Oligonucleotides and Analogues, A Practical Approach*, IRL Press at Oxford University Press; Baserga and Denhardt, eds., 1992, *Antisense Strategies, Annals of the New York Academy of Sciences*, Volume 600, NYAS; Milligan et al., 1993, *J. Med. Chem.* 36(14):1923–1937; *Antisense Research and Applications*, 1993, CRC Press, in its entirety and specifically Chapter 15, by Sanghvi, entitled "Heterocyclic base modifications in nucleic acids and their applications in antisense oligonucleotides;" and Sudhir Agrawal, ed., 1996, *Antisense Therapeutics*, Humana Press, Totowa, N.J., all of which are incorporated by reference.

D. Labeled Antisense Oligonucleotides

It is often useful to label the antisense polynucleotides of the invention, for example, when the ADNF III polynucleotides are to be used for detection of ADNF III expression, or for the diagnosis and prognosis of conditions related to pathological hyperproliferation. The labels may be incorporated by any of a number of means well known to those of skill in the art. Suitable labels are any composition detectable by spectroscopic, photochemical, biochemical, immunochemical, or chemical means. For example, useful labels include $^{32}P$, $^{35}S$, fluorescent dyes, electron-dense reagents, enzymes (e.g., as commonly used in an ELISA), biotin-streptavadin, digoxigenin, haptens and proteins for which antisera or monoclonal antibodies are available, or nucleic acid molecules with a sequence complementary to a target. The label often generates a measurable signal, such as radioactivity, that can be used to quantitate the amount of bound detectable moiety.

The label can be incorporated in or attached to a polynucleotide either covalently, or through ionic, van der Waals or hydrogen bonds, e.g., incorporation of radioactive nucleotides, or biotinylated nucleotides that are recognized by streptavadin. The detectable moiety may be directly or indirectly detectable. Indirect detection can involve the binding of a second directly or indirectly detectable moiety to the detectable moiety. For example, the detectable moiety can be the ligand of a binding partner, such as biotin, which is a binding partner for streptavadin, or a nucleotide sequence, which is the binding partner for a complementary sequence, to which it can specifically hybridize. The binding partner may itself be directly detectable, for example, an antibody may be itself labeled with a fluorescent molecule. The binding partner also may be indirectly detectable, for example, a nucleic acid having a complementary nucleotide sequence can be a part of a branched DNA molecule that is in turn detectable through hybridization with other labeled nucleic acid molecules.

V. Administration of ADNF III Antisense Oligonucleotides

A. Enhancing Cellular Uptake of Oligonucleotides

An important factor in the use of antisense compounds, such as antisense oligonucleotides, is the ability of such compounds to traverse the plasma membrane of a cell, or the membrane of an intra-cellular compartment, such as the nucleus.

Oligonucleotides can be administered to cells as naked nucleic acid suspended in a suitable standard buffer. Such oligonucleotides may enter the cell by freely traversing the cell membrane, by phagocytosis, or by other cellular mechanisms.

Oligonucleotides can also be linked to a compound that aids in membrane translocation, e.g., a polypeptide, nucleic acid, lipid, or other suitable compounds known to those of skill in the art.

Proteins have been described that have the ability to translocate across a cell membrane. Typically, such proteins have amphiphilic or hydrophobic subsequences that have the ability to act as membrane-translocating carriers. For example, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, 1996, *Current Opinion in Neurobiology* 6:629–634. Another subsequence, the h (hydrophobic) domain of signal peptides, was found to have similar cell membrane translocation characteristics (see, e.g., Lin et al., 1995, *J. Biol. Chem.* 270:14255–14258).

Such subsequences can be used to translocate oligonucleotides across a cell membrane. Oligonucleotides can be conveniently derivatized with such sequences. For example, a linker can be used to link the oligonucleotides and the translocation sequence. Any suitable linker can be used, e.g., a peptide linker or any other suitable chemical linker.

Examples of peptide sequences which can be linked to oligonucleotides of the invention, such as for facilitating uptake of oligonucleotides into cells, include, but are not limited to: an 11 amino acid peptide of the tat protein of HIV; a 20 residue peptide sequence which corresponds to amino acids 84–103 of the p16 protein (see Fahraeus et al., 1996, *Current Biology* 6:84); the third helix of the 60 amino acid long homeodomain of Antennapedia (Derossi et al., 1994, *J. Biol. Chem.* 269:10444) or the h region of a signal peptide such as the Kaposi fibroblast growth factor (K-FGF) h region (Lin et al., supra). Other suitable chemical moieties that provide enhanced cellular uptake may also be chemically linked to suitable oligonucleotides.

Oligonucleotides are also introduced into a mammalian cell by a transfection method. In an embodiment, the transfection methods comprise: (1) forming a transfection complex consisting essentially of oligonucleotide, and a lipid component consisting essentially of a neutral and/or cationic lipid, optionally including a quartenary ammonium detergent and/or a lipopolyamine, optionally including a polycation (poly lysine, polyarginine, and the like), optionally including a receptor-recognition molecule that binds to a predetermined cell surface receptor (e.g., asialoglycoprotein receptor), and (2) contacting cells with the transfection complex, which can be in vitro, ex vivo, or in vivo.

In embodiments where a receptor recognition protein is included in the transfection complex, cells expressing the predetermined cell surface receptor are mixed with a composition comprising the receptor-recognition transfection complex under physiological transfection conditions which permit uptake of the oligonucleotides into said cells.

Polynucleotides can be linked to either end of the oligonucleotides of the invention. Such polynucleotides can also enhance cellular uptake. In one variation, the charged backbone of the linked polynucleotide enhances binding to cationic lipids, and facilitates formation and/or stability or other desired properties of oligonucleotide: lipid delivery complexes. Oligonucleotide:lipid delivery complexes include, but are not limited to: liposomes comprising oligonucleotides, immunoliposomes comprising oligonucleotides, cationic lipid:oligonucleotide aggregates, polylysine:lipid:oligonucleotide complexes, polyarginine:lipid:oligonucleotide complexes, receptor recognition protein (rrP):polylysine:lipid:oligonucleotide complexes, receptor recognition protein (rrP):polyarginine:lipid:oligonucleotide complexes and the like.

B. Pharmaceutical Compositions

Pharmaceutically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present invention (see, e.g., *Remington's Pharmaceutical Sciences*, 17$^{th}$ ed., 1989).

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

In the practice of this invention, compositions can be administered, for example, by intravenous infusion, orally, topically, intraperitoneally, intravesically or intrathecally. Parenteral administration and intravenous administration are the preferred methods of administration. The formulations of commends can be presented in unit-dose or multi-dose sealed containers, such as ampules and vials. Injection solutions and suspensions can be prepared from sterile powders, granules, and tablets of the kind previously described.

The dose administered to a patient, in the context of the present invention, should be sufficient to effect a beneficial therapeutic response in the patient over time. The dose will be determined by the efficacy of the particular oligonucleotide employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In therapeutic applications, the ADNF III antisense oligonucleotides of the invention are administered, e.g., to a cancer patient, in an amount sufficient to inhibit growth of pathologically proliferating cells, e.g., cancer cells. An amount adequate to accomplish this is defined as a "therapeutically effective dose." Amounts effective for this use will depend on, for example, the particular ADNF III oligonucleotide employed, the type of cancer to be treated, the manner of administration, the weight and general state of health of the patient, and the judgment of the prescribing physician. The physician typically also evaluates circulating plasma levels of the oligonucleotide, vector toxicities, progression of the disease, and the production of anti-vector or oligonucleotide antibodies. In general, the dose equivalent of a naked nucleic acid from a vector is from about 1 $\mu$g to 100 $\mu$g for a typical 70 kilogram patient, and doses of vectors are calculated to yield an equivalent amount of therapeutic nucleic acid.

For administration, compounds of the present invention can be administered at a rate determined by the LD-50 of the vector or oligonucleotide, and the side-effects of the oligonucleotide or vector at various concentrations, as applied to the mass and overall health of the patient. Administration can be accomplished via single or divided doses or, e.g., by administration to the site of a solid tumor in a slow release container.

C. Administration of Antisense Oligonucleotides

For a pharmaceutical composition, the antisense oligonucleotides of the methods of the invention can be inserted into any of a number of well-known vectors for the transfection of target cells and organisms. For example, nucleic acids are delivered as DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see Anderson, 1992, *Science* 256:808–813; Nabel & Felgner, 1993, *TIBTECH* 11:211–217; Mitani & Caskey, 1993, *TIBTECH* 11:162–166; Dillon, 1993, *TIBTECH* 11:167–175; Miller, 1992, *Nature* 357:455–460; Van Brunt, 1988, *Biotechnology* 6(10): 1149–1154; Vigne, 1995, *Restorative Neurology and Neuroscience* 8:35–36; Kremer & Perricaudet, 1995, *British Medical Bulletin* 51(1):31–44; Yu et al., 1994, *Gene Therapy* 1:13–26; Haddada et al., 1995, in *Current Topics in Microbiology and Immunology*, Doerfler and Böhm, eds.

Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in, e.g., U.S. Pat. Nos. 5,049,386, 4,946,787, and 4,897,355. Llipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

All publications and patent applications cited in this specification are herein incorporated by reference as if each individual publication or patent specification were specifically and individually indicated to be incorporated by reference.

VI. EXAMPLES

Although the foregoing invention is described in some detail by way of illustration and example for purposes of clarity of understanding, it will be readily apparent to one of ordinary skill in light of the teachings of this invention that a variety of noncritical parameters could be changed or modified to yield essentially similar results without departing from the spirit or scope of the appended claims.

Example I
Detection of hADNF III Expression in Human Tissues

To characterize human ADNF III (hADNF III) expression, dot blot hybridization was performed on a representative array of human RNA samples from multiple tissues. Human RNA master blot—PT3004-1 was purchased from Clontech, Palo Alto, Calif., USA and probed with hADNF III as described in Bassan et al., 1999, *J. Neurochem.* 72: 1283–93 (FIG. 1). Results indicated enriched expression in brain areas including the cerebellum, frontal lobe, hippocampus, medula oblangata, subthalamic nuclei, and in proliferating cells (e.g. immune cells) and glandular tissues like the thyroid gland and the thymus. The transcript was barely detectable in the adult liver and lung. It was increased in the fetal liver (2.4-times) and increased in the fetal lung (5-times) and placenta.

The localization of hADNF III mRNA to brain structures, glandular tissues and dividing cells indicates a role in cell proliferation. Since hADNF III is highly expressed in some embryonic tissues but is essentially undetectable in the corresponding adult tissues, it might be a developmental regulatory factor. Based on cDNA and deduced protein sequence (U.S. Ser. No. 09/267,511, filed Mar. 12, 1999), hADNF III might be a transcription factor associated with cell division. The thiotransferase/glutaredoxin active site found in hADNF III (FIG. 4) may modulate DNA binding activity of itself or of transcription factors in response to oxidative stress and signal transduction pathways associated with the redox state of the cell. One hypothesis may involve a protein with 7 putative initiator methionine residues at the N-terminal of the protein (FIG. 4) and processing pathways that may yield secreted portions.

Example II
Chromosomal Localization of hADNF III

Chromosomal localization of hADNF III was determined using the following methods: 1) radiation hybrid mapping (Stanford Human Genome Center), 2) fluorescent in situ hybridization (FISH) with a genomic human contig (including hADNF III, Sanger genome center, dJ914P20 contig ID 02099, The Sanger Blast Server). Utilizing these public data bases, results were obtained localizing the gene to chromosome 20q13.2 [with identity to the ordered markers: G30243, W45435 in linkage to the genome data base (GDB) locus D20S831] and to 20q13.13–13.2 utilizing a human contig sequence containing the hADNF III gene.

It is possible that hADNF III is a member of a family of genes spread across the chromosomal region 20q12–13.2, since it is not usual for the signal in FISH to be spread to this extent. In this respect, this chromosomal region is amplified in many tumors. In breast tumors, comparative genomic hybridization revealed approximately 20 regions of recurrent increased DNA sequence copy number (Kallioniemi et al., 1994, Proc. Natl. Acad. Sci. USA, 91:2156–60; Isola et al., 1995, Am. J. Path., 147: 905–11). The chromosomal 20q13 region is likely to harbor novel oncogenes, the overexpression of which, as a result of the amplification, contributes to cancer progression.

In this respect, ADNF III gene expression was augmented in the presence of the neuropeptide, vasoactive intestinal peptide (VIP). VIP receptors have been suggested as human tumor markers, and VIP antagonists inhibit embryonic and tumor growth (see, Gressens et al, 1993, Nature 362:155–158; Virgolini et al., 1997, Eur. J. Clin. Invest. 27:793–800; Moody et al., 1993, Proc. Natl. Acad. Sci. USA 90:4345–4349; Lilling et al., 1995, J. Molec. Neurosci. 5:231–239). VIP has also been implicated as a neuronal survival factor, inhibiting neurodegeneration in vitro (Brenneman et al., 1986, Proc. Natl. Acad. Sci. USA 83:1159–1162) and in vivo (Gozes et al., 1996, Proc. Natl. Acad. Sci. USA 93:427–432). It is possible that ADNF III mediates, in part, the VIP growth stimulation and neuroprotective effects. Thus, these results suggest that ADNF III is important for cell survival.

One cDNA clone containing hADNF III also included the TBP1 protein downstream of the coding region of ADNF III. Previously, the TBP1 gene was localized to chromosome 11p12–p1317 and the TBP1 gene product was associated with cell cycle. This finding may indicate translocation involved with cancer formation and propagation.

Example III
Detection of Altered hADNF III Expression in Human Cancers

As the chromosomal region 20q12–20q13 is amplified in a wide variety of tumors, the association of hADNF III with cancer growth was investigated by quantitating hADNF III mRNA in human primary cancer tissue (breast and colon) in comparison to adjacent normal tissue.

RNA was extracted from human primary tumors and adjacent normal tissue obtained fresh, post surgery, and frozen on liquid nitrogen immediately (breast and colon, five patients). RNA was also extracted from a neuroblastoma cell line, NMB (N) (Lilling et al., 1995, J. Molec. Neurosci. 5: 231–39). Total RNA was prepared from human tissues and cells by extracting with RNAzol B solution (Tel-Test, Inc., Friendwood, Tex., USA).

The RNA (10–12 $\mu$g) was subjected to electrophoresis followed by Northern blot hybridization on Nitran 0, 45 filters (Schleicher and Schuell, Dasssel, Germany). The cloned ADNF III (FIG. 4) with the primers 5'-ATCTGTAGGCCAGGGTTACA-3' (SEQ ID NO:9) and 5'-TTGAGGAAGTGTTACCTGGG-3' (SEQ ID NO:10), sense and antisense, respectively (1005–1024, sense; 1308–1327, antisense, FIG. 4) was subjected to PCR using AmpliTaq DNA Polymerase (Perkin Elmer, Branchburg, N.J., USA) and—$^{32}$P-dCTP (Amersham, 3000 Ci/mmol) and used as a probe. Ribosomal RNA stained with ethidium bromide and actin mRNA were used as an internal standards.

Figure 3:
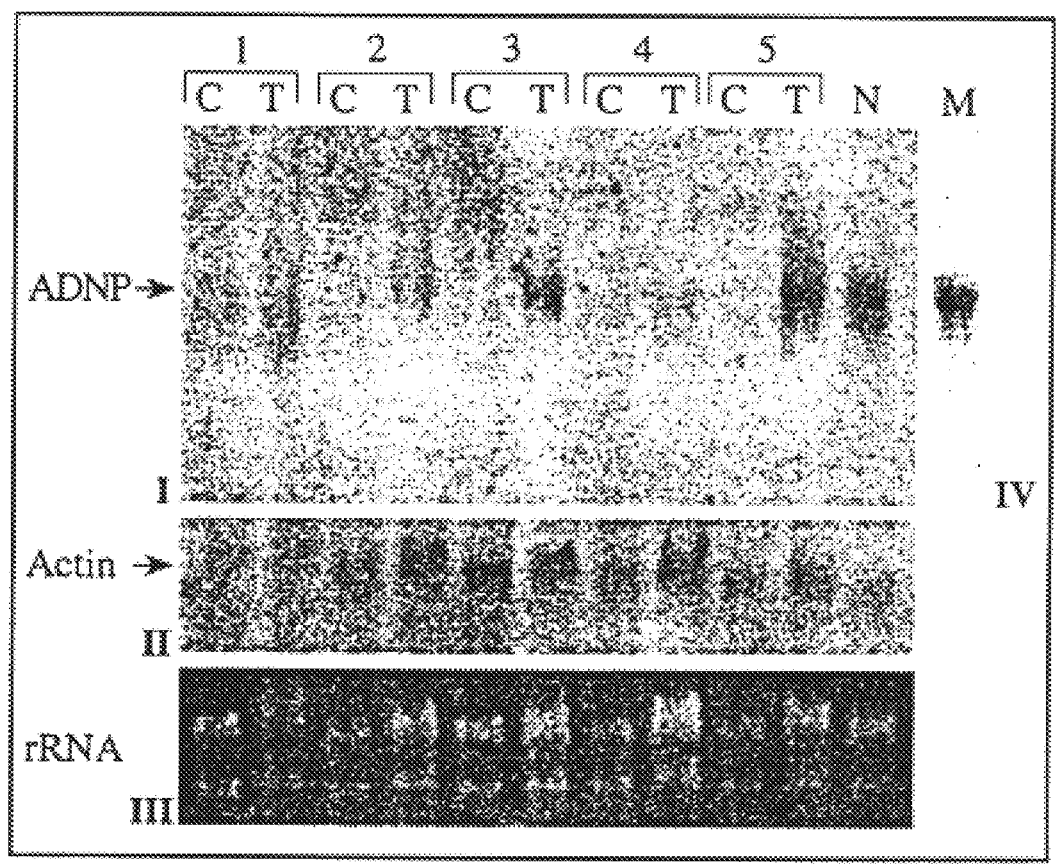
FIG. 3 shows that the human ADNF III mRNA is increased in tumors. N=neuroblastoma cell line (as described in Lilling et al., 1995, *J. Molec. Neurosci.* 5: 231–39); M=mouse brain ADNF III mRNA; C=control tissue; T=tumor. 1 and 4 are colon cancer adenocarcinoma; 2, 3 and 5 are breast cancer. The figure shows autoradiograms I, II and IV and ethidium bromide staining, III. The same blots were subjected to actin hybridization as a control.

Northern blot hybridization identified one major mRNA band (5.5 kb, FIG. 3). Furthermore, this mRNA was enriched in mouse hippocampus and cerebellum and augmented in the presence of the neuropeptide, vasoactive intestinal peptide (VIP), in rat cerebral cortical astrocytes.

Expression of hADNF III is increased in the cancer (FIG. 3). The increase was most evident with breast cancer and ranged 14.4±4.6 fold (mean±SEM). When the ADNF III mRNA content was compared to actin mRNA content, in the same samples, the increase ranged 10.9±5 fold.

Example IV
Inhibition of Growth of Cancer Cells Using Selected hADNF III Antisense Oligodeoxynucleotides A. Selection and synthesis of antisense oligodeoxynucleotides For growth inhibition experiments, six antisense oligodeoxynucleotides were synthesized (FIG. 4). The oligodeoxynucleotides were chosen as complementary to the most 5' methionines of the largest protein coding exon (3800 bp) in hADNF III. The antisense oligodeoxynucleotide sequences used in growth inhibition experiments were: TTGACAGGAAGTTGGAACAT (SEQ ID NO:1); GCTTCATAGGACTTTGGCAT (SEQ ID NO:2); ATCCTTGGTGGGAGTCCCAT (SEQ ID NO:3); TGAGAGTCGATTCACC (SEQ ID NO:4); CAGATGAACACTGGACAT (SEQ ID NO:5); and ACCTAGACCCAGTCTCAT (SEQ ID NO:6).

B. Cell culture and treatment with antisense hADNFIII oligonucleotides

The human colon cancer cell line HT-29 was cultured in Dulbecco-modified Eagle's medium (DMEM) supplemented with 10% heat inactivated fetal calf serum (FCS), 2 mM L-glutamine and 1% Pen-Strep-Nystatin (Biological Industries, Beit Haemek, Israel). The adherent cells were split when a sub-confluent monolayer was formed following trypsin/EDTA treatment (0.25 units/0.02%) and naturalization with serum containing medium. Sub-confluent adherent cells were washed with phosphate-buffered saline (PBS), treated with trypsin as above and re-suspended in DMEM containing 5% FCS to a final concentration of 50,000 cells/ml. 100 $\mu$l aliquots were seeded into individual wells of a 96-well microtiter plates (Nunclon, Nunc Brand Products, Roskilde, Denmark). Each plate had a blank column and the appropriate controls. Plates were incubated for 24 hours in a humidified atmosphere containing 95% air/5% $CO_2$, at 37°

C., medium was then replaced to contain an antisense oligodeoxynucleotide at a concentration of 10 μM in DMEM without FCS. Following an additional one day incubation period the medium was replaced again to contain DMEM/ 5% FCS and cells were subjected to a further 48 hours incubation period before quantitation of cell growth.

C. Inhibition of cancer cell growth

Viable cell number was determined by a 3 hour incubation with the MTS reagent (CellTiter 96 AQ$_{ueous}$ cell proliferation kit, Promega, Madison Wis., USA). The MTS reagent is oxidized by active mitochondria, resulting in increases in light absorbance at 490 nm (evaluated by a multiscan plate reader). For statistical analysis, ANOVA with Student-Neuman-Kuels multiple comparison of means test was used to assess the results.

Figure 5:
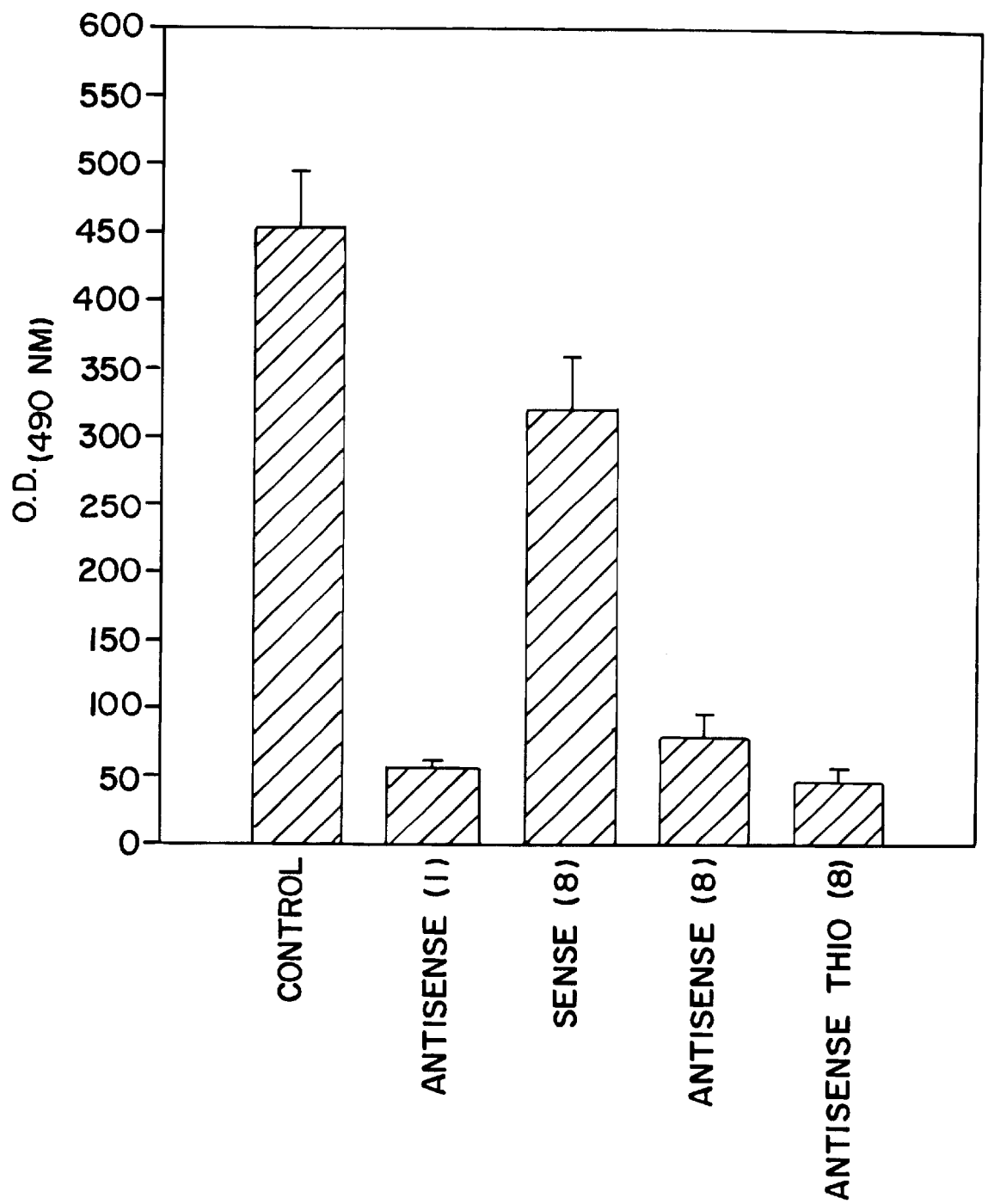
FIG. 5 illustrates that HT-29 cell growth is inhibited in the presence of antisense oligodeoxynucleotides specific for human ADNF III mRNA. Six antisense oligodeoxynucleotides were synthesized and utilized to inhibit cancer growth. A representative figure is shown with antisense oligodeoxynucleotides 1 and 8.

The antisense oligodeoxynucleotides 1 (SEQ ID NO:1) and 8 (SEQ ID NO:2) inhibited cell division of the human intestinal cancer, HT-29, by 90% (FIG. 5, $P<0.001$). Furthermore, the antisense oligodeoxynucleotide 9 (SEQ ID NO:3) inhibited cell growth by about 37.5±3%, and the antisense oligodeoxynucleotide 68 (SEQ ID NO:6) also inhibited growth, by 45±3% ($P<0.001$). In contrast to oligodeoxynucleotides 8 and 9, the sequence of oligodeoxynucleotide 68 is shared by other cDNA sequences, hence may not be specific. Further specificity was determined with a control sense oligodeoxynucleotide complementary to antisense 8 and with an antisense 8 with all internucleotide bonds of the phosphorothioated type (FIG. 5, thio).

The antisense oligodeoxynucleotides 7 (SEQ ID NO:4) and 67 (SEQ ID NO:5) did not inhibit growth.

Vasoactive intestinal peptide (VIP) receptor has been found to be a marker for tumors such as gastrointestinal neuroendocrine cancers, and colonic and pancreatic adenocarcinomas (see, Virgolini et al., 1994, *New Eng. J. Med.* 331:1116; Virgolini et al., 1998, *J. Nucl. Med.* 39:1575; Raderer et al., 1998, *J. Nucl. Med.* 39:1570; Virgolini, 1997, *Eur. J. Clin. Invest.* 27:793). Other studies have identified a very high incidence of VIP receptor binding in breast, ovarian, endometrial, prostate, bladder, lung, esophageal, colonic, and pancreatic tumors, as well as neuroendocrine and brain tumors (Reubi, 1996, *Ann. NY Acad. Sci. USA* 805:753). In view of the preponderance of tumors containing VIP receptors, intervention with tumor growth may employ a gene down-stream of VIP action that is directly associated with stimulation of cell proliferation and survival. The fact that ADNF III gene expression was augmented in the presence of VIP indicates that ADNF III antisense oligonucleotides present a way of inhibiting a multiplicity of tumors.

What is claimed is:

1. A method of inhibiting the growth of a cancer cell, the method comprising the step of contacting the cell with an ADNFIII antisense oligonucleotide that is fully complementary to a subsequence of an ADNFIII nucleic acid, wherein the antisense oligonucleotide is selected from the group consisting of SEQ ID NO: 1, SEQ ID NO: 2, SEQ ID NO: 3 and SEQ ID NO: 6.

2. The method of claim 1, wherein the ADNF III nucleic acid is an mRNA.

3. The method of claim 1, wherein the cell is contacted with the antisense oligonucleotides at a concentration of 10 µM.

4. The method of claim 1, wherein the ADNF III nucleic acid is a human ADNF III nucleic acid.

5. The method of claim 4, wherein the ADNF III nucleic acid encodes a protein comprising (SEQ ID NO:8).

6. The method of claim 5, wherein the antisense ADNF III nucleic acid has the nucleotide sequence comprising (SEQ ID NO:7).

7. The method of claim 1, wherein the antisense oligonucleotide is selected from the group consisting of a DNA oligonucleotide, a peptide nucleic acid oligonucleotide, a phosphorothioate oligonucleotide, and a 2'-O methyl oligonucleotide.

8. The method of claim 1, wherein the antisense oligonucleotide is about 8 to about 50 nucleotides in length.

9. The method of claim 8, wherein the antisense oligonucleotide is about 15 to about 25 nucleotides in length.

10. The method of claim 1, wherein the antisense oligonucleotide is a ribozyme.

11. The method of claim 1, wherein the cell is a cancer cell.

12. The method of claim 11, wherein the cancer cell is selected from the group consisting of breast cancer, neuroblastoma, ovarian cancer, endometrial cancer, prostate cancer, bladder cancer, lung cancer, esophageal cancer, neuroendocrine cancer, brain cancer, colon cancer, testicular cancer, pancreatic cancer, and leukemia.

13. The method of claim 1, wherein the cell is contacted with two or more antisense oligonucleotides complementary to different subsequences of an ADNF III nucleic acid.

* * * * *

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:antisense
      oligonucleotide 1

<400> SEQUENCE: 1
ttgacaggaa gttggaacat                                                   20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:antisense
      oligonucleotide 8

<400> SEQUENCE: 2
gcttcatagg actttggcat                                                   20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:antisense
      oligonucleotide 9

<400> SEQUENCE: 3
atccttggtg ggagtcccat                                                   20

<210> SEQ ID NO 4
<211> LENGTH: 16
<212> TYPE: DNA
```

```
<213> ORGANISM: Artificial Sequence
<220> FEATURE:
<223> OTHER INFORMATION: Description of Artificial Sequence:antisense
      oligonucleotide 7

<400> SEQUENCE: 4
tgagagtcga ttcacc                                                    16

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:antisense
      oligonucleotide 67

<400> SEQUENCE: 5
cagatgaaca ctggacat                                                  18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence:antisense
      oligonucleotide 68

<400> SEQUENCE: 6
acctagaccc agtctcat                                                  18

<210> SEQ ID NO 7
<211> LENGTH: 4386
<212> TYPE: DNA
<213> ORGANISM: Homo sapiens
<220> FEATURE:
<223> OTHER INFORMATION: human activity dependent neurotrophic factor
      III (ADNF III) cDNA
<220> FEATURE:
<221> NAME/KEY: CDS
<222> LOCATION: (1)..(3309)
<223> OTHER INFORMATION: hADNF III

<400> SEQUENCE: 7 atg ttc caa ctt cct gtc aac aat ctt ggc agt tta aga aaa gcc cgg     48
Met Phe Gln Leu Pro Val Asn Asn Leu Gly Ser Leu Arg Lys Ala Arg
 1               5                  10                  15 aaa act gtg aaa aaa ata ctt agt gac att ggg ttg gaa tac tgt aaa     96
Lys Thr Val Lys Lys Ile Leu Ser Asp Ile Gly Leu Glu Tyr Cys Lys
            20                  25                  30 gaa cat ata gaa gat ttt aaa caa ttt gaa cct aat gac ttt tat ttg    144
Glu His Ile Glu Asp Phe Lys Gln Phe Glu Pro Asn Asp Phe Tyr Leu
        35                  40                  45 aaa aac act aca tgg gag gat gta gga ctg tgg gac cca tca ctt acg    192
Lys Asn Thr Thr Trp Glu Asp Val Gly Leu Trp Asp Pro Ser Leu Thr
    50                  55                  60 aaa aac cag gac tat cgg aca aaa cct ttc tgc tgc agc gct tgt cca    240
Lys Asn Gln Asp Tyr Arg Thr Lys Pro Phe Cys Cys Ser Ala Cys Pro
65                  70                  75                  80 ttt tcc tca aaa ttc ttc tct gcc tac aaa agt cat ttc cgc aat gtc    288
Phe Ser Ser Lys Phe Phe Ser Ala Tyr Lys Ser His Phe Arg Asn Val
                85                  90                  95 cat agt gaa gac ttt gaa aat agg att ctc ctt aat tgc ccc tac tgt    336
His Ser Glu Asp Phe Glu Asn Arg Ile Leu Leu Asn Cys Pro Tyr Cys
            100                 105                 110 acc ttc aat gca gac aaa aag act ttg gaa aca cac att aaa ata ttt    384
```

```
                -continued

Thr Phe Asn Ala Asp Lys Lys Thr Leu Glu Thr His Ile Lys Ile Phe
        115                 120                 125 cat gct ccg aac gcc agc gca cca agt agc agc ctc agc act ttc aaa      432
His Ala Pro Asn Ala Ser Ala Pro Ser Ser Ser Leu Ser Thr Phe Lys
        130                 135                 140 gat aaa aac aaa aat gat ggc ctt aaa cct aag cag gct gac agt gta      480
Asp Lys Asn Lys Asn Asp Gly Leu Lys Pro Lys Gln Ala Asp Ser Val
145                 150                 155                 160 gag caa gct gtt tat tac tgt aag aag tgc act tac cga gat cct ctt      528
Glu Gln Ala Val Tyr Tyr Cys Lys Lys Cys Thr Tyr Arg Asp Pro Leu
                165                 170                 175 tat gaa ata gtt agg aag cac att tac agg gaa cat ttt cag cat gtg      576
Tyr Glu Ile Val Arg Lys His Ile Tyr Arg Glu His Phe Gln His Val
            180                 185                 190 gca gca cct tac ata gca aag gca gga gaa aaa tca ctc aat ggg gca      624
Ala Ala Pro Tyr Ile Ala Lys Ala Gly Glu Lys Ser Leu Asn Gly Ala
        195                 200                 205 gtc ccc tta ggc tcg aat gcc cga gaa gag agt agt att cac tgc aag      672
Val Pro Leu Gly Ser Asn Ala Arg Glu Glu Ser Ser Ile His Cys Lys
    210                 215                 220 cga tgc ctt ttc atg cca aag tcc tat gaa gct ttg gta cag cat gtc      720
Arg Cys Leu Phe Met Pro Lys Ser Tyr Glu Ala Leu Val Gln His Val
225                 230                 235                 240 atc gaa gac cat gaa cgt ata ggc tat cag gtc act gcc atg att ggg      768
Ile Glu Asp His Glu Arg Ile Gly Tyr Gln Val Thr Ala Met Ile Gly
                245                 250                 255 cac aca aat gta gtg gtt ccc cga tcc aaa ccc ttg atg cta att gct      816
His Thr Asn Val Val Val Pro Arg Ser Lys Pro Leu Met Leu Ile Ala
            260                 265                 270 ccc aaa cct caa gac aag aag agc atg gga ctc cca cca agg atc ggt      864
Pro Lys Pro Gln Asp Lys Lys Ser Met Gly Leu Pro Pro Arg Ile Gly
        275                 280                 285 tcc ctt gct tct gga aat gtc cgg tct tta cca tca cag cag atg gtg      912
Ser Leu Ala Ser Gly Asn Val Arg Ser Leu Pro Ser Gln Gln Met Val
    290                 295                 300 aat cga ctc tca ata cca aag cct aac tta aat tct aca gga gtc aac      960
Asn Arg Leu Ser Ile Pro Lys Pro Asn Leu Asn Ser Thr Gly Val Asn
305                 310                 315                 320 atg atg tcc agt gtt cat ctg cag cag aac aac tat gga gtc aaa tct     1008
Met Met Ser Ser Val His Leu Gln Gln Asn Asn Tyr Gly Val Lys Ser
                325                 330                 335 gta ggc cag ggt tac agt gtt ggt cag tca atg aga ctg ggt cta ggt     1056
Val Gly Gln Gly Tyr Ser Val Gly Gln Ser Met Arg Leu Gly Leu Gly
            340                 345                 350 ggc aac gca cca gtt tcc att cct caa caa tct cag tct gta aag cag     1104
Gly Asn Ala Pro Val Ser Ile Pro Gln Gln Ser Gln Ser Val Lys Gln
        355                 360                 365 tta ctt cca agt gga aac gga agg tct tat ggg ctt ggg tca gag cag     1152
Leu Leu Pro Ser Gly Asn Gly Arg Ser Tyr Gly Leu Gly Ser Glu Gln
    370                 375                 380 agg tcc cag gca cca gca aga tac tcc ctg cag tct gct aat gcc tct     1200
Arg Ser Gln Ala Pro Ala Arg Tyr Ser Leu Gln Ser Ala Asn Ala Ser
385                 390                 395                 400 tct ctc tca tcg ggc cag tta aag tct cct tcc ctc tct cag tca cag     1248
Ser Leu Ser Ser Gly Gln Leu Lys Ser Pro Ser Leu Ser Gln Ser Gln
                405                 410                 415 gca tcc aga gtg tta ggt cag tcc agt tcc aaa cct gct gca gct gcc     1296
Ala Ser Arg Val Leu Gly Gln Ser Ser Ser Lys Pro Ala Ala Ala Ala
            420                 425                 430
```

```
aca ggc cct ccc cca ggt aac act tcc tca act caa aag tgg aaa ata      1344
Thr Gly Pro Pro Pro Gly Asn Thr Ser Ser Thr Gln Lys Trp Lys Ile
        435                 440                 445 tgt aca atc tgt aat gag ctt ttt cct gaa aat gtc tat agt gtg cac      1392
Cys Thr Ile Cys Asn Glu Leu Phe Pro Glu Asn Val Tyr Ser Val His
450                 455                 460 ttc gaa aaa gaa cat aaa gct gag aaa gtc cca gca gta gcc aac tac      1440
Phe Glu Lys Glu His Lys Ala Glu Lys Val Pro Ala Val Ala Asn Tyr
465                 470                 475                 480 att atg aaa ata cac aat ttt act agc aaa tgc ctc tac tgt aat cgc      1488
Ile Met Lys Ile His Asn Phe Thr Ser Lys Cys Leu Tyr Cys Asn Arg
                485                 490                 495 tat tta ccc aca gat act ctg ctc aac cat atg tta att cat ggt ctg      1536
Tyr Leu Pro Thr Asp Thr Leu Leu Asn His Met Leu Ile His Gly Leu
        500                 505                 510 tct tgt cca tat tgc cgt tca act ttc aat gat gtg gaa aag atg gcc      1584
Ser Cys Pro Tyr Cys Arg Ser Thr Phe Asn Asp Val Glu Lys Met Ala
        515                 520                 525 gca cac atg cgg atg gtt cac att gat gaa gag atg gga cct aaa aca      1632
Ala His Met Arg Met Val His Ile Asp Glu Glu Met Gly Pro Lys Thr
530                 535                 540 gat tct act ttg agt ttt gat ttg aca ttg cag cag ggt agt cac act      1680
Asp Ser Thr Leu Ser Phe Asp Leu Thr Leu Gln Gln Gly Ser His Thr
545                 550                 555                 560 aac atc cat ctc ctg gta act aca tac aat ctg agg gat gcc cca gct      1728
Asn Ile His Leu Leu Val Thr Thr Tyr Asn Leu Arg Asp Ala Pro Ala
                565                 570                 575 gaa tct gtt gct tac cat gcc caa aat aat cct cca gtt cct cca aag      1776
Glu Ser Val Ala Tyr His Ala Gln Asn Asn Pro Pro Val Pro Pro Lys
        580                 585                 590 cca cag cca aag gtt cag gaa aag gca gat atc cct gta aaa agt tca      1824
Pro Gln Pro Lys Val Gln Glu Lys Ala Asp Ile Pro Val Lys Ser Ser
        595                 600                 605 cct caa gct gca gtg ccc tat aaa aaa gat gtt ggg aaa acc ctt tgt      1872
Pro Gln Ala Ala Val Pro Tyr Lys Lys Asp Val Gly Lys Thr Leu Cys
        610                 615                 620 cct ctt tgc ttt tca atc cta aaa gga ccc ata tct gat gca ctt gca      1920
Pro Leu Cys Phe Ser Ile Leu Lys Gly Pro Ile Ser Asp Ala Leu Ala
625                 630                 635                 640 cat cac tta cga gag agg cac caa gtt att cag acg gtt cat cca gtt      1968
His His Leu Arg Glu Arg His Gln Val Ile Gln Thr Val His Pro Val
                645                 650                 655 gag aaa aag ctc acc tac aaa tgt atc cat tgc ctt ggt gtg tat acc      2016
Glu Lys Lys Leu Thr Tyr Lys Cys Ile His Cys Leu Gly Val Tyr Thr
        660                 665                 670 agc aac atg acc gcc tca act atc act ctg cat cta gtt cac tgc agg      2064
Ser Asn Met Thr Ala Ser Thr Ile Thr Leu His Leu Val His Cys Arg
        675                 680                 685 ggc gtt gga aag acc caa aat ggc cag gat aag aca aat gca ccc tct      2112
Gly Val Gly Lys Thr Gln Asn Gly Gln Asp Lys Thr Asn Ala Pro Ser
690                 695                 700 cgg ctt aat cag tct cca agt ctg gca cct gtg aag cgc act tac gag      2160
Arg Leu Asn Gln Ser Pro Ser Leu Ala Pro Val Lys Arg Thr Tyr Glu
705                 710                 715                 720 caa atg gaa ttt ccc tta ctg aaa aaa cga aag tta gat gat gat agt      2208
Gln Met Glu Phe Pro Leu Leu Lys Lys Arg Lys Leu Asp Asp Asp Ser
                725                 730                 735 gat tca ccc agc ttc ttt gaa gag aag cct gaa gag cct gtt gtt tta      2256
Asp Ser Pro Ser Phe Phe Glu Glu Lys Pro Glu Glu Pro Val Val Leu
        740                 745                 750
```

```
gct tta gac ccc aag ggt cat gaa gat gat tcc tat gaa gcc agg aaa    2304
Ala Leu Asp Pro Lys Gly His Glu Asp Asp Ser Tyr Glu Ala Arg Lys
        755                 760                 765 agc ttt cta aca aag tat ttc aac aaa cag ccc tat ccc acc agg aga    2352
Ser Phe Leu Thr Lys Tyr Phe Asn Lys Gln Pro Tyr Pro Thr Arg Arg
    770                 775                 780 gaa att gag aag cta gca gcc agt tta tgg tta tgg aag agt gac atc    2400
Glu Ile Glu Lys Leu Ala Ala Ser Leu Trp Leu Trp Lys Ser Asp Ile
785                 790                 795                 800 gct tcc cat ttt agt aac aaa agg aag aag tgt gtc cgt gat tgt gaa    2448
Ala Ser His Phe Ser Asn Lys Arg Lys Lys Cys Val Arg Asp Cys Glu
            805                 810                 815 aag tac aag cct ggc gtg ttg ctg ggg ttt aac atg aaa gaa tta aat    2496
Lys Tyr Lys Pro Gly Val Leu Leu Gly Phe Asn Met Lys Glu Leu Asn
        820                 825                 830 aaa gtc aag cat gag atg gat ttt gat gct gag tgg cta ttt gaa aat    2544
Lys Val Lys His Glu Met Asp Phe Asp Ala Glu Trp Leu Phe Glu Asn
    835                 840                 845 cat gat gag aag gat tcc aga gtc aat gct agt aag act gct gac aaa    2592
His Asp Glu Lys Asp Ser Arg Val Asn Ala Ser Lys Thr Ala Asp Lys
850                 855                 860 aag ctc aac ctt ggg aag gaa gat gac agt tcc tca gac agt ttt gaa    2640
Lys Leu Asn Leu Gly Lys Glu Asp Asp Ser Ser Ser Asp Ser Phe Glu
865                 870                 875                 880 aat ttg gaa gaa gaa tcc aat gaa agt ggt agc cct ttt gac cct gtt    2688
Asn Leu Glu Glu Glu Ser Asn Glu Ser Gly Ser Pro Phe Asp Pro Val
            885                 890                 895 ttt gaa gtt gaa cct aaa atc tct aac gat aac cca gag gaa cat gta    2736
Phe Glu Val Glu Pro Lys Ile Ser Asn Asp Asn Pro Glu Glu His Val
        900                 905                 910 ctg aag gta att cct gag gat gct tca gaa tct gag gag aag cta gac    2784
Leu Lys Val Ile Pro Glu Asp Ala Ser Glu Ser Glu Glu Lys Leu Asp
    915                 920                 925 caa aaa gag gat ggt tca aaa tac gaa act att cat ttg act gag gaa    2832
Gln Lys Glu Asp Gly Ser Lys Tyr Glu Thr Ile His Leu Thr Glu Glu
930                 935                 940 cca acc aaa cta atg cac aat gca tct gat agt gag gtt gac caa gac    2880
Pro Thr Lys Leu Met His Asn Ala Ser Asp Ser Glu Val Asp Gln Asp
945                 950                 955                 960 gat gtt gtt gag tgg aaa gac ggt gct tct cca tct gag agt ggg cct    2928
Asp Val Val Glu Trp Lys Asp Gly Ala Ser Pro Ser Glu Ser Gly Pro
            965                 970                 975 gga tcc caa caa gtg tca gac ttt gag gac aat acc tgc gaa atg aaa    2976
Gly Ser Gln Gln Val Ser Asp Phe Glu Asp Asn Thr Cys Glu Met Lys
        980                 985                 990 cca gga acc tgg tct gac gag tct tcc caa agc gaa gat gca agg agc    3024
Pro Gly Thr Trp Ser Asp Glu Ser Ser Gln Ser Glu Asp Ala Arg Ser
    995                 1000                1005 agt aag cca gct gcc aaa aaa aag gct acc atg caa ggt gac aga gag    3072
Ser Lys Pro Ala Ala Lys Lys Lys Ala Thr Met Gln Gly Asp Arg Glu
    1010                1015                1020 cag ttg aaa tgg aag aat agt tcc tat gga aaa gtt gaa ggg ttt tgg    3120
Gln Leu Lys Trp Lys Asn Ser Ser Tyr Gly Lys Val Glu Gly Phe Trp
1025                1030                1035                1040 tct aag gac cag tca cag tgg aag aat gca tct gag aat gat gag cgc    3168
Ser Lys Asp Gln Ser Gln Trp Lys Asn Ala Ser Glu Asn Asp Glu Arg
                1045                1050                1055 tta tct aac ccc cag att gag tgg cag aat agc aca att gac agt gag    3216
Leu Ser Asn Pro Gln Ile Glu Trp Gln Asn Ser Thr Ile Asp Ser Glu
```

```
                    1060              1065              1070
gat ggg gaa cag ttt gac aac atg act gat gga gta gct gag ccc atg      3264
Asp Gly Glu Gln Phe Asp Asn Met Thr Asp Gly Val Ala Glu Pro Met
       1075              1080              1085 cat ggc agc tta gcc gga gtt aaa ctg agc agc caa cag gcc              3306
His Gly Ser Leu Ala Gly Val Lys Leu Ser Ser Gln Gln Ala
   1090              1095              1100 taagtgccag gttccctggc attggtgaca tgctgcagcc tggaactctg atctccagtg    3366
tgactgcaaa gctgtcttct cactggtact gccttgtgag tactggttgg actgtggggc    3426
atgtggccgc tgcagttcca gtggttattt ctaagtctat gacaggacag gctgttcttg    3486
cttcagaacc ttctctgaca gacacggtaa ctaaatgtga aaaaccaata agctggtgac    3546
tcatgaatac acacgaggaa agcagaggt ttattttatc tgccttttca acatttcttt     3606
ccctctgtga aatgattggt cagatgtctt tgagaagtgt taaactaatt cacatggtag    3666
tgtagggcca acatacaagc taccagtcta atgtgtatag tagactttgg gaaaagcgat    3726
ttttttttcat gtattcattc tgaatagttg aaatgtatat ttgtacagtc ttttagacct   3786
attcaagtga tgctcatgat cctgttactg tgtgcccatc atagatttct tttttagtg     3846
ttgcccttgc tgtgtaataa acgctctatc tagtttacct agcaaaagct caaaactgcg    3906
ctagtatgga cttttggac agacttagtt tttgcacata accttgtaca atcttgcaac     3966
agaggccagc cacgtaagat atatatctgg actctcttgt attataggat ttttcttgtt    4026
ctgaatatcc ttgacattac agctgtcaaa acaaaaact ggtatttcag atctgttttc     4086
tgaaatcttt taagctaaaa tcacatgcaa gaattgactt tgcagctact aattttgaca    4146
cctttagat ctgtataaaa gtgtgttgtg ttgaagcagc aaaccaatga gtgctgcatt     4206
ttggatattt agtttatct ttagttcaac accatcatgg tggattcatt tataccatct     4266
aatatatgac acactgttgt agtatgtata attttgtgat ctttattttc cctttgtatt    4326
cattttaagc atctaaataa attgctgtat tgtgcttaat gtaaaaaaaa aaaaaaaaa     4386

<210> SEQ ID NO 8
<211> LENGTH: 1102
<212> TYPE: PRT
<213> ORGANISM: Homo sapiens
<220> FEATURE:
<223> OTHER INFORMATION: human activity dependent neurotrophic factor
      III (ADNF III) cDNA

<400> SEQUENCE: 8

Met Phe Gln Leu Pro Val Asn Asn Leu Gly Ser Leu Arg Lys Ala Arg
  1               5                  10                  15

Lys Thr Val Lys Lys Ile Leu Ser Asp Ile Gly Leu Glu Tyr Cys Lys
             20                  25                  30

Glu His Ile Glu Asp Phe Lys Gln Phe Glu Pro Asn Asp Phe Tyr Leu
         35                  40                  45

Lys Asn Thr Thr Trp Glu Asp Val Gly Leu Trp Asp Pro Ser Leu Thr
     50                  55                  60

Lys Asn Gln Asp Tyr Arg Thr Lys Pro Phe Cys Cys Ser Ala Cys Pro
 65                  70                  75                  80

Phe Ser Ser Lys Phe Phe Ser Ala Tyr Lys Ser His Phe Arg Asn Val
                 85                  90                  95

His Ser Glu Asp Phe Glu Asn Arg Ile Leu Leu Asn Cys Pro Tyr Cys
            100                 105                 110

Thr Phe Asn Ala Asp Lys Lys Thr Leu Glu Thr His Ile Lys Ile Phe
```

-continued

```
            115                 120                 125
His Ala Pro Asn Ala Ser Ala Pro Ser Ser Ser Leu Ser Thr Phe Lys
    130                 135                 140

Asp Lys Asn Lys Asn Asp Gly Leu Lys Pro Lys Gln Ala Asp Ser Val
145                 150                 155                 160

Glu Gln Ala Val Tyr Tyr Cys Lys Lys Cys Thr Tyr Arg Asp Pro Leu
                165                 170                 175

Tyr Glu Ile Val Arg Lys His Ile Tyr Arg Glu His Phe Gln His Val
            180                 185                 190

Ala Ala Pro Tyr Ile Ala Lys Ala Gly Glu Lys Ser Leu Asn Gly Ala
        195                 200                 205

Val Pro Leu Gly Ser Asn Ala Arg Glu Glu Ser Ile His Cys Lys
210                 215                 220

Arg Cys Leu Phe Met Pro Lys Ser Tyr Glu Ala Leu Gln His Val
225                 230                 235                 240

Ile Glu Asp His Glu Arg Ile Gly Tyr Gln Val Thr Ala Met Ile Gly
                245                 250                 255

His Thr Asn Val Val Pro Arg Ser Lys Pro Leu Met Leu Ile Ala
            260                 265                 270

Pro Lys Pro Gln Asp Lys Lys Ser Met Gly Leu Pro Pro Arg Ile Gly
        275                 280                 285

Ser Leu Ala Ser Gly Asn Val Arg Ser Leu Pro Ser Gln Gln Met Val
    290                 295                 300

Asn Arg Leu Ser Ile Pro Lys Pro Asn Leu Asn Ser Thr Gly Val Asn
305                 310                 315                 320

Met Met Ser Ser Val His Leu Gln Gln Asn Asn Tyr Gly Val Lys Ser
                325                 330                 335

Val Gly Gln Gly Tyr Ser Val Gly Gln Ser Met Arg Leu Gly Leu Gly
            340                 345                 350

Gly Asn Ala Pro Val Ser Ile Pro Gln Gln Ser Gln Ser Val Lys Gln
        355                 360                 365

Leu Leu Pro Ser Gly Asn Gly Arg Ser Tyr Gly Leu Gly Ser Glu Gln
    370                 375                 380

Arg Ser Gln Ala Pro Ala Arg Tyr Ser Leu Gln Ser Ala Asn Ala Ser
385                 390                 395                 400

Ser Leu Ser Ser Gly Gln Leu Lys Ser Pro Ser Leu Ser Gln Ser Gln
                405                 410                 415

Ala Ser Arg Val Leu Gly Gln Ser Ser Lys Pro Ala Ala Ala Ala
            420                 425                 430

Thr Gly Pro Pro Gly Asn Thr Ser Ser Thr Gln Lys Trp Lys Ile
        435                 440                 445

Cys Thr Ile Cys Asn Glu Leu Phe Pro Glu Asn Val Tyr Ser Val His
    450                 455                 460

Phe Glu Lys Glu His Lys Ala Glu Lys Val Pro Ala Val Ala Asn Tyr
465                 470                 475                 480

Ile Met Lys Ile His Asn Phe Thr Ser Lys Cys Leu Tyr Cys Asn Arg
                485                 490                 495

Tyr Leu Pro Thr Asp Thr Leu Leu Asn His Met Leu Ile His Gly Leu
            500                 505                 510

Ser Cys Pro Tyr Cys Arg Ser Thr Phe Asn Asp Val Glu Lys Met Ala
        515                 520                 525

Ala His Met Arg Met Val His Ile Asp Glu Glu Met Gly Pro Lys Thr
    530                 535                 540
```

-continued

```
Asp Ser Thr Leu Ser Phe Asp Leu Thr Leu Gln Gln Gly Ser His Thr
545                 550                 555                 560

Asn Ile His Leu Leu Val Thr Thr Tyr Asn Leu Arg Asp Ala Pro Ala
                565                 570                 575

Glu Ser Val Ala Tyr His Ala Gln Asn Asn Pro Val Pro Pro Lys
            580                 585                 590

Pro Gln Pro Lys Val Gln Glu Lys Ala Asp Ile Pro Val Lys Ser Ser
        595                 600                 605

Pro Gln Ala Ala Val Pro Tyr Lys Lys Asp Val Gly Lys Thr Leu Cys
        610                 615                 620

Pro Leu Cys Phe Ser Ile Leu Lys Gly Pro Ile Ser Asp Ala Leu Ala
625                 630                 635                 640

His His Leu Arg Glu Arg His Gln Val Ile Gln Thr Val His Pro Val
                645                 650                 655

Glu Lys Lys Leu Thr Tyr Lys Cys Ile His Cys Leu Gly Val Tyr Thr
                660                 665                 670

Ser Asn Met Thr Ala Ser Thr Ile Thr Leu His Leu Val His Cys Arg
            675                 680                 685

Gly Val Gly Lys Thr Gln Asn Gly Gln Asp Lys Thr Asn Ala Pro Ser
        690                 695                 700

Arg Leu Asn Gln Ser Pro Ser Leu Ala Pro Val Lys Arg Thr Tyr Glu
705                 710                 715                 720

Gln Met Glu Phe Pro Leu Leu Lys Lys Arg Lys Leu Asp Asp Asp Ser
                725                 730                 735

Asp Ser Pro Ser Phe Phe Glu Glu Lys Pro Glu Glu Pro Val Val Leu
            740                 745                 750

Ala Leu Asp Pro Lys Gly His Glu Asp Asp Ser Tyr Glu Ala Arg Lys
            755                 760                 765

Ser Phe Leu Thr Lys Tyr Phe Asn Lys Gln Pro Tyr Pro Thr Arg Arg
        770                 775                 780

Glu Ile Glu Lys Leu Ala Ala Ser Leu Trp Leu Trp Lys Ser Asp Ile
785                 790                 795                 800

Ala Ser His Phe Ser Asn Lys Arg Lys Lys Cys Val Arg Asp Cys Glu
                805                 810                 815

Lys Tyr Lys Pro Gly Val Leu Leu Gly Phe Asn Met Lys Glu Leu Asn
            820                 825                 830

Lys Val Lys His Glu Met Asp Phe Asp Ala Glu Trp Leu Phe Glu Asn
            835                 840                 845

His Asp Glu Lys Asp Ser Arg Val Asn Ala Ser Lys Thr Ala Asp Lys
850                 855                 860

Lys Leu Asn Leu Gly Lys Glu Asp Asp Ser Ser Ser Asp Ser Phe Glu
865                 870                 875                 880

Asn Leu Glu Glu Glu Ser Asn Glu Ser Gly Ser Pro Phe Asp Pro Val
                885                 890                 895

Phe Glu Val Glu Pro Lys Ile Ser Asn Asp Asn Pro Glu Glu His Val
            900                 905                 910

Leu Lys Val Ile Pro Glu Asp Ala Ser Glu Ser Glu Lys Leu Asp
        915                 920                 925

Gln Lys Glu Asp Gly Ser Lys Tyr Glu Thr Ile His Leu Thr Glu Glu
        930                 935                 940

Pro Thr Lys Leu Met His Asn Ala Ser Asp Ser Glu Val Asp Gln Asp
945                 950                 955                 960
```

-continued

```
Asp Val Val Glu Trp Lys Asp Gly Ala Ser Pro Ser Glu Ser Gly Pro
                965                 970                 975

Gly Ser Gln Gln Val Ser Asp Phe Glu Asp Asn Thr Cys Glu Met Lys
            980                 985                 990

Pro Gly Thr Trp Ser Asp Glu Ser Ser Gln Ser Glu Asp Ala Arg Ser
        995                 1000                1005

Ser Lys Pro Ala Ala Lys Lys Ala Thr Met Gln Gly Asp Arg Glu
    1010                1015                1020

Gln Leu Lys Trp Lys Asn Ser Ser Tyr Gly Lys Val Glu Gly Phe Trp
1025                1030                1035                1040

Ser Lys Asp Gln Ser Gln Trp Lys Asn Ala Ser Glu Asn Asp Glu Arg
                1045                1050                1055

Leu Ser Asn Pro Gln Ile Glu Trp Gln Asn Ser Thr Ile Asp Ser Glu
            1060                1065                1070

Asp Gly Glu Gln Phe Asp Asn Met Thr Asp Gly Val Ala Glu Pro Met
        1075                1080                1085

His Gly Ser Leu Ala Gly Val Lys Leu Ser Ser Gln Gln Ala
    1090                1095                1100

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:sense primer

<400> SEQUENCE: 9
atctgtaggc cagggttaca                                                  20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:antisense
      primer

<400> SEQUENCE: 10
ttgaggaagt gttacctggg                                                  20
```